(12) United States Patent
Sum et al.

(10) Patent No.: US 10,538,540 B2
(45) Date of Patent: Jan. 21, 2020

(54) PEROVSKITE CORE-SHELL NANOCRYSTALS

(71) Applicant: NANYANG TECHNOLOGICAL UNIVERSITY, Singapore (SG)

(72) Inventors: Tze Chien Sum, Singapore (SG); Weiqiang Chen, Singapore (SG); Subodh Gautam Mhaisalkar, Singapore (SG); Nripan Mathews, Singapore (SG); Sjoerd Antonius Veldhuis, Singapore (SG); Saikat Bhaumik, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 15/637,385

(22) Filed: Jun. 29, 2017

(65) Prior Publication Data

US 2018/0002354 A1    Jan. 4, 2018

(30) Foreign Application Priority Data

Jun. 29, 2016    (SG) .............................. 10201605333T

(51) Int. Cl.
C07F 7/24    (2006.01)
C07F 7/08    (2006.01)
G01N 21/64    (2006.01)

(52) U.S. Cl.
CPC .............. *C07F 7/24* (2013.01); *C07F 7/0834* (2013.01); *C01P 2002/01* (2013.01);
(Continued)

(58) Field of Classification Search
None
See application file for complete search history.

(56) References Cited

U.S. PATENT DOCUMENTS

2017/0346024 A1* 11/2017 Lee ..................... H01L 51/0077

FOREIGN PATENT DOCUMENTS

WO    WO-2016072806    * 5/2016    ............. C09K 11/02

OTHER PUBLICATIONS

Bhaumik et al. Chem Commun, 2016, 52, 7118.*
(Continued)

*Primary Examiner* — Clinton A Brooks
(74) *Attorney, Agent, or Firm* — Sughrue Mion, PLLC

(57) ABSTRACT

Provided is a nanocrystal comprising a core comprised in a shell, wherein the core comprises a first material of a perovskite structure comprising a first organic cation not exceeding a molar weight of about 45 g/mol, a first divalent metal and a first counter anion, and, wherein the shell comprises a second material of a perovskite structure comprising a second organic cation having a molar weight between about 74 g/mol and about 187 g/mol, optionally the first organic cation, a second divalent metal and a second counter anion. Provided is further a matrix having the nanocrystal as defined above encapsulated therein. Provided is further a process for the synthesis of a nanocrystal comprising a core comprised in a shell, the process comprising a) preparing a precursor solution containing at least one divalent metal, a first organic cation not exceeding a molar weight of about 45 g/mol, a second organic cation having a molar weight between about 74 g/mol and about 187 g/mol, and at least one counter anion in a polar aprotic solvent; and b) subjecting the precursor solution to a nonpolar solvent to form the nanocrystal.

19 Claims, 28 Drawing Sheets

(52) U.S. Cl.
CPC ...... *C01P 2002/34* (2013.01); *C01P 2002/70* (2013.01); *C01P 2002/84* (2013.01); *G01N 2021/6417* (2013.01)

(56) References Cited

OTHER PUBLICATIONS

Sani et al. Materials. 2018, 11, 1008.*
Kojima et al., "Organometal Halide Perovskites as Visible-Light Sensitizers for Photovoltaic Cells", J. Am. Chem. Soc., vol. 131, No. 17, 2009, pp. 6050-6051. (2 pages total).
Kim et al., "Lead Iodide Perovskite Sensitized All-Solid-State Submicron Thin Film Mesoscopic Solar Cell with Efficiency Exceeding 9%", Scientific Reports, vol. 2, No. 591, Aug. 21, 2012, pp. 1-7. (7 pages total).
Burschka et al., "Sequential Deposition as a Route to High-Performance Perovskite-Sensitized Solar Cells", Nature, vol. 499, Jul. 18, 2013, pp. 316-319. (5 pages total).
Liu et al., "Efficient Planar Heterojunction Perovskite Solar Cells by Vapour Deposition", Nature, vol. 501, Sep. 19, 2013, pp. 395-398. (8 pages total).
Jeon et al., "Solvent Engineering for High-Performance Inorganic—Organic Hybrid Perovskite Solar Cells", Nature Materials, vol. 13, Sep. 2014, pp. 897-903. (7 pages total).
Bi et al., "Efficient Luminescent Solar Cells Based on Tailored Mixed-Cation Perovskites", Sci. Adv., vol. 2, Ed. 1501170, Jan. 1, 2016, pp. 1-7. (7 pages total).
Tan et al., "Bright Light-Emitting Diodes Based on Organometal Halide Perovskite", Nature Nanotechnology, vol. 9, Sep. 2014, pp. 687-692. (6 pages total).
Xing et al. "Low-Temperature Solution-Processed Wavelength-Tunable Perovskites for Lasing", Nature Materials, vol. 13, May 2014, pp. 476-480. (5 pages total).
Bade et al., "Fully Printed Halide Perovskite Light-Emitting Diodes with Silver Nanowire Electrodes", ACS Nano, vol. 10, 2016, pp. 1795-1801. (7 pages total).
Cho et al., "Overcoming the Electroluminescence Efficiency Limitations of Perovskite Light-Emitting Diodes", Science, vol. 350, Issue 6265; Dec. 4, 2015, pp. 1222-1225. (5 pages total).
Yantara et al., "Inorganic Halide Perovskites for Efficient Light-Emitting Diodes", J. Phys. Chem. Lett., vol. 6, Oct. 16, 2015, pp. 4360-4364. (5 pages total).

Shirasaki et al., "Emergence of Colloidal Quantum-Dot Light-Emitting Technologies", Nature Photonics, vol. 7, Jan. 2013, pp. 13-23. (11 pages total).
Protesescu et al., "Nanocrystals of Cesium Lead Halide Perovskites ($CsPbX_3$, X = Ci, Br, and I): Novel Optoelectronic Materials Showing Bright Emission with Wide Color Gamut", Nano Letters, vol. 15, 2015, pp. 3692-3696. (5 pages total).
Zhang et al., "Brightly Luminescent and Color-Tunable Colloidal $CH_3NH_3PbX_3$ (X = Br, I, Ci) Quantum Dots: Potential Alternatives for Display Technology", ACS Nano, vol. 9, No. 4, 2015, pp. 4533-4542. (10 pages total).
Gonzales-Carrero et al., "Organic-Inorganic and All-Inorganic Lead Halide Nanoparticles [Invited]", Optics Express, vol. 24, No. 2, Jan. 25, 2016, pp. A285-A301, (17 pages total).
Gonzalez-Carrero et al., "Maximizing the Emissive Properties of $CH_3NH_3PbBr_3$ Perovskite Nanoparticles", Journal of Materials Chemistry A, vol. 3, 2015, pp. 9187-9193. (7 pages total).
Huang et al., "Control of Emission Color of High Quantum Yield $CH_3NH_3PbBr_3$ Perovskite Quantum Dots by Precipitation Temperature", Advanced Science, vol. 2, 2015, pp. 1-5. (5 pages total).
Xie et al., "Synthesis and Characterization of Highly Luminescent CdSe-Core $CdS/Zn_{0.5}Cd_{0.5}S/ZnS$ Multishell Nanocrystals", J. Am. Chem. Soc., vol. 127, 2005, pp. 7480-7488. (9 pages total).
Tyagi et al., "Colloidal Organohalide Perovskite Nanoplatelets Exhibiting Quantum Confinement", J. Phys. Chem. Lett., vol. 6, 2015, pp. 1911-1916. (6 pages total).
Zhang et al., "Composition-Dependent Photoluminescence Intensity and Prolonged Recombination Lifetime of Perovskite $CH_3NH_3PbBr_{3-x}Ci_x$ Films", Chem. Commun., vol. 50, 2014, pp. 11727-11730. (4 pages total).
Tabuchi et al., "Preparation and Characterization of Natural Lower Dimensional Layered Perovskite-Type Compounds", Journal of Physics and Chemistry of Solids, vol. 61, 2000, pp. 837-845. (9 pages total).
Pathak et al., "Perovskite Crystals for Tunable White Light Emission", Chemistry of Materials, vol. 27, 2015, pp. 8066-8075. (10 pages total).
Sichert et al., "Quantum Size Effect in Organometal Halide Perovskite Nanoplatelets", Nano Letters, vol. 15, 2015, pp. 6521-6527. (7 pages total).
Mitzi, "Templating and Structural Engineering in Organic—Inorganic Perovskites", J. Chem. Soc., Dalton Trans., 2001, pp. 1-12. (12 pages total).
Yuan et al., A Facile One-Pot Synthesis of Deep Blue Luminescent Lead Bromide Perovskite Microdisks, Chem. Commun., vol. 51, 2015, pp. 16385-16388. (4 pages total).

* cited by examiner

Fig. 23

| MPPL / P-NCs | 800 nm (2PA) | 1200 nm (3PA) | 1600 nm (4PA) | 2100 nm (5PA) |
|---|---|---|---|---|
| MAPbBr$_3$ core-only NCs | | | | |
| MAPbBr$_3$/(OA)$_2$PbBr$_4$ core-shell NCs | | | | |
| CsPbBr$_3$ NCs | | | | |

PEROVSKITE CORE-SHELL NANOCRYSTALS

CROSS-REFERENCE TO RELATED APPLICATION

This application claims the benefit of priority of Singapore Patent Application No. 10201605333T, filed Jun. 29, 2016, the contents of it being hereby incorporated by reference in its entirety for all purposes.

TECHNICAL FIELD

The present disclosure refers generally to the field of nanocrystals, in particular organic-inorganic quantum dots having a core-shell structure, which have the structure of perovskite.

Their nonlinear optical properties makes them a suitable material for optical limiting, bioimaging and low-threshold upconversion lasing applications.

BACKGROUND

Low-temperature solution-processed organic-inorganic halide perovskites have demonstrated striking performance in photon harvesting photovoltaics with efficiencies exceeding 22.1%. Additionally, these hybrid materials have displayed great potential for light-emitting applications as a result of their large optical absorption, high photoluminescence quantum yield (PLQY). Especially, the colloidal nanocrystals (NCs) of organic-inorganic and all-inorganic halide perovskites have exhibited further improved light-emitting performance due to the quantum confinement effect, which results in increased PLQY, tunable optical bandgap and PL wavelength.

In comparison to the conventional II-VI group semiconductor nanocrystals (like CdSe), the halide perovskite nanocrystals exhibits one to two orders larger one-photon absorption cross-sections, resulting from the stronger light-matter interactions in the perovskite NCs. Such strong light-matter interactions imply large nonlinear optical properties (especially multiphoton absorption) of the perovskite NCs, which is essential for applications in optical-limiting, multiphoton microscopy for deep tissue imaging and low-threshold upconversion lasing.

Materials or devices possessing large transmission at low incident light intensity/fluence, while exhibiting small transmission at high incident light intensity/fluence are referred as optical limiters. In the optical limiters, the light transmission decreases nonlinearly as the incident intensity/fluence increases, and drops significantly when the intensity/fluence of the incident radiation exceeds a certain threshold, the optical limiting threshold. As per convention, the intensity/fluence at which the light transmission decreases to 50% of the linear transmittance is defined as the limiting threshold. In accordance with such intriguing properties observed in optical limiters, they are valuable for protecting optical sensors, human eyes and other light-detecting objects, which may suffer from damages resulting from direct exposure to strong light sources such as pulsed lasers. Although NCs of certain metals and metal oxides possess optical limiting properties, they are not suitable for use in short laser pulses with nanosecond or femtosecond pulse widths. Optical limiting materials based on two-photon absorption (TPA) with large TPA properties and thus low-limiting threshold have been demonstrated to be appropriate for optically limiting nanosecond or femtosecond pulsed lasers.

In contrast to linear emission results from one-photon absorption, upconversion PL excited by simultaneous multiphoton absorption possesses essential merits for deep tissue imaging, including higher spatial resolution, larger penetration depth, less light scattering and less damage to the investigated samples. Furthermore, in contrast with the upconversion PL excited by lower-order nonlinear optical absorption, the four- and five-photon absorption processes with four- and five-order dependence on the incident light intensity/fluence can provide much stronger spatial confinement, resulting in much higher contrast in imaging.

However, due to the low transition probabilities of the four- and five-photon absorption processes in both organic molecules and conventional inorganic semiconductors, it is notoriously difficult to observe their related phenomenon.

Multiphoton pumped upconversion lasing not only possesses all the above merits of upconversion PL, but is also valuable for applications in effective frequency upconversion and short-pulse optical communications, owing to its coherent nature and the merit of no requirement for phase-matching conditions. Since large enough multiphoton absorption is required to achieve population inversion in the gain medium, realizing multiphoton pumped lasing is more challenging and difficult than the upconversion PL.

In this context, core and core-shell type organic-inorganic perovskite NCs with different sizes and shapes are targeted as competitive optical limiting materials working in the short laser pulses region (nanosecond and femtosecond), due to their excellent two-photon absorption properties. Importantly, owing to their large multiphoton absorption and high PLQY, these samples are also applied for achieving efficient multiphoton excited upconversion PL and low-threshold upconversion lasing.

Organic-inorganic hybrid halide perovskite materials have already revolutionized solar cell applications. The certified power conversion efficiency of solar cells based on $CH_3NH_3PbI_3$ and derivatives have reached a record value of 20.8% within a short period. Concurrently, the potential of perovskites to transform the field of light emission has been demonstrated. The focus has now been expanded to encompass the fabrication of perovskite nanocrystals (NCs) to achieve color tunability and enhanced PLQYs. It appears that even a slight change in the synthetic protocol can significantly influence the band-gap tuning, size, ordering and photophysical properties of the nanocrystals. For example, the Perez-Prieto group reported a non-template strategy for the synthesis of colloidal methylammonium lead bromide ($MAPbBr_3$) nanocrystals with a particle size of around 6 nm showing a photoluminescence quantum yield (PLQY) of up to 83%, whereas the Dong group reported a ligand-assisted re-precipitation strategy (LARP) for the synthesis of $MAPbBr_3$ nanocrystals (NCs) with a particle size of around 3.3 nm and photoluminescence quantum yield (PLQY) between 50 and 93%. Despite these promising results, efforts have not been made to improve luminescence stability in parallel with enhancing the PL efficiency.

It is therefore an object of the present disclosure to provide a material with nonlinear optical properties showing upconversion photoluminescence excited by simultaneous multiphoton absorption. It is also an object of the present disclosure to provide a material with a high quantum yield which remains stable over a long time.

SUMMARY

In a first aspect, the present disclosure refers to a nanocrystal comprising a core comprised in a shell, wherein the core comprises a first material of a perovskite structure comprising a first organic cation not exceeding a molar weight of about 45 g/mol, a first divalent metal and a first counter anion, and wherein the shell comprises a second material of a perovskite structure comprising a second organic cation having a molar weight between about 74 g/mol and about 187 g/mol, optionally the first organic cation, a second divalent metal and a second counter anion.

One of the methods to enhance the stability, efficiency and brightness of semiconductor nanocrystals is by growing a shell of a larger band-gap semiconductor around it. Such nanocrystals with small regions of one material embedded in another with a wider band gap are known as core-shell semiconducting nanocrystals (CSSNCs). This type of crystal engineering improves the quantum yield of the nanocrystals by confining charge carriers, passivating non-radiative recombination sites and making them more robust to processing conditions.

Advantageously, in 2-dimensional layered perovskites like for example (octylammonium)$_2$PbBr$_4$, the inorganic metal halide layers are separated by the large organic cations (octylammonium), which results in a large d-spacing. The varied d-spacings point to the co-crystallization tendency of the organic ammonium perovskites. The high photoluminescence quantum yield (PLQY) and stability of the nanocrystals could possibly be explained by the formation of such a mixed organic shell. Both the enhanced PLQY and the improved stability are achieved by coating a perovskite core comprising a first, small organic cation not exceeding a molar weight of 45 g/mol, a first divalent metal and a first counter anion, with a layered perovskite shell comprising a second, large organic cation having a molar weight between 74 g/mol and 187 g/mol, optionally the first organic cation, a second divalent metal and a second counter anion. Thus, the ensuing core-shell nanocrystal not only provides dielectric confinement, but also effective surface passivation.

In a second aspect, the present disclosure refers to a matrix having a nanocrystal as described above encapsulated therein. Advantageously, by encapsulating the nanocrystal in a matrix, stability may be further enhanced and/or cytotoxicity may be reduced.

In a third aspect, the present disclosure refers to a process for the synthesis of a nanocrystal comprising a core comprised in a shell, the process comprising a) preparing a precursor solution containing a first, divalent metal, a first organic cation not exceeding a molar weight of about 45 g/mol, a second organic cation having a molar weight between about 74 g/mol and about 187 g/mol, and a first and second counter anion in a polar aprotic solvent; and b) subjecting the precursor solution to a non-polar solvent to form the nanocrystal comprising a core comprised in a shell. Advantageously, the process provides core-shell nanocrystals, wherein the core and the shell is formed in 'one-pot' approach.

In a fourth aspect, the present disclosure refers to a use of the core-shell nanocrystal as described above for optical limiting, bioimaging and upconversion lasing application.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments are described with reference to the following drawings.

FIG. 23 show photographs of luminescence from MAPbBr$_3$, MAPbBr$_3$/(OA)$_2$PbBr$_4$ and CsPbBr$_3$ NCs at 800, 1200, 1600 and 2100 nm femtosecond laser excitation.

The almost flat open-aperture Z-scan curve of toluene under the same excitation condition (with peak intensity of ~50.0 GW cm$^{-2}$) is also shown; (d) Open-aperture Z-scan responses from CsPbBr$_3$ NCs (~1.0 μM) under laser excitation with peak intensities of ~35.0 and ~50.0 GW cm$^{-2}$.

Figure 27:
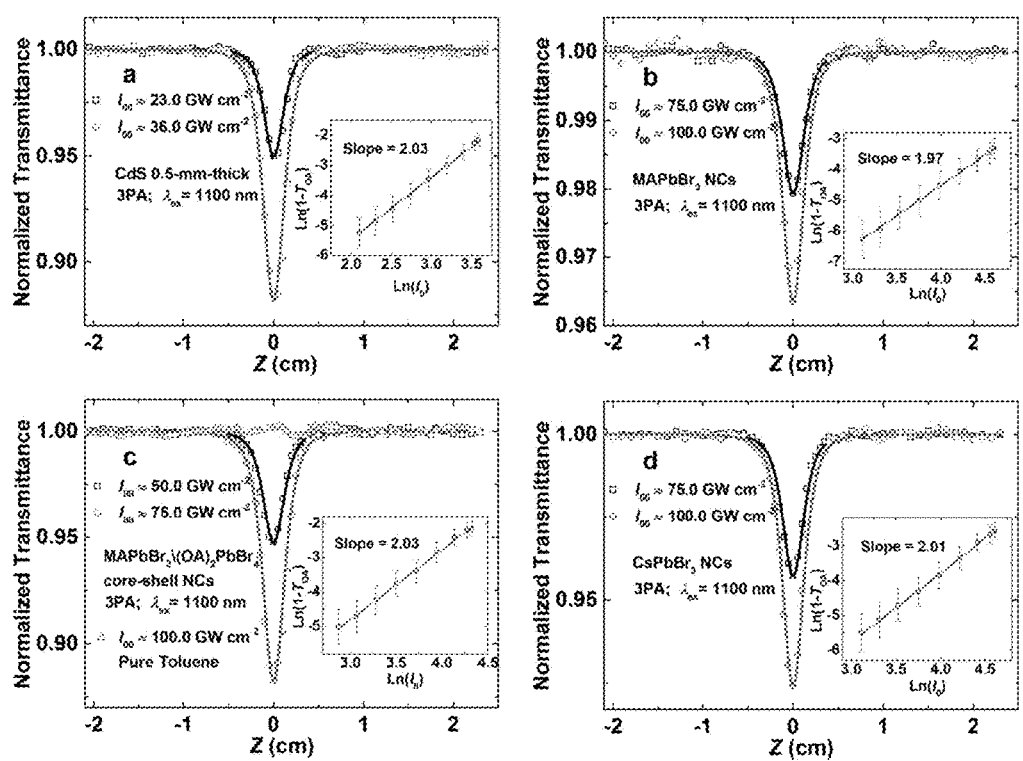

FIG. 27 shows open-aperture Z-scan measurements on 3 PA in perovskite NCs at 1100 nm (a) Open-aperture Z-scan curves of the standard sample CdS (0.5-mm thick) at 1100 nm with excitation peak intensities of ~23.0 and ~36.0 GW cm$^{-2}$; (b) Open-aperture Z-scan responses from the toluene solutions of MAPbBr$_3$ NCs (~2.0 μM) contained in 1-mm-thick cuvette under laser excitation with peak intensities of ~75.0 and ~100.0 GW cm$^{-2}$; (c) Open-aperture Z-scan responses from MAPbBr$_3$/(OA)$_2$PbBr$_4$ NCs (~2.1 μM) excited with peak intensities of ~50.0 and ~75.0 GW cm$^{-2}$. The almost flat open-aperture Z-scan curve of toluene under the same excitation condition (with peak intensity of ~100.0 GW cm$^{-2}$) is also shown; (d) Open-aperture Z-scan responses from CsPbBr$_3$ NCs (~1.0 μM) under laser excitation with peak intensities of ~75.0 and ~100.0 GW cm$^{-2}$.

Figure 28:
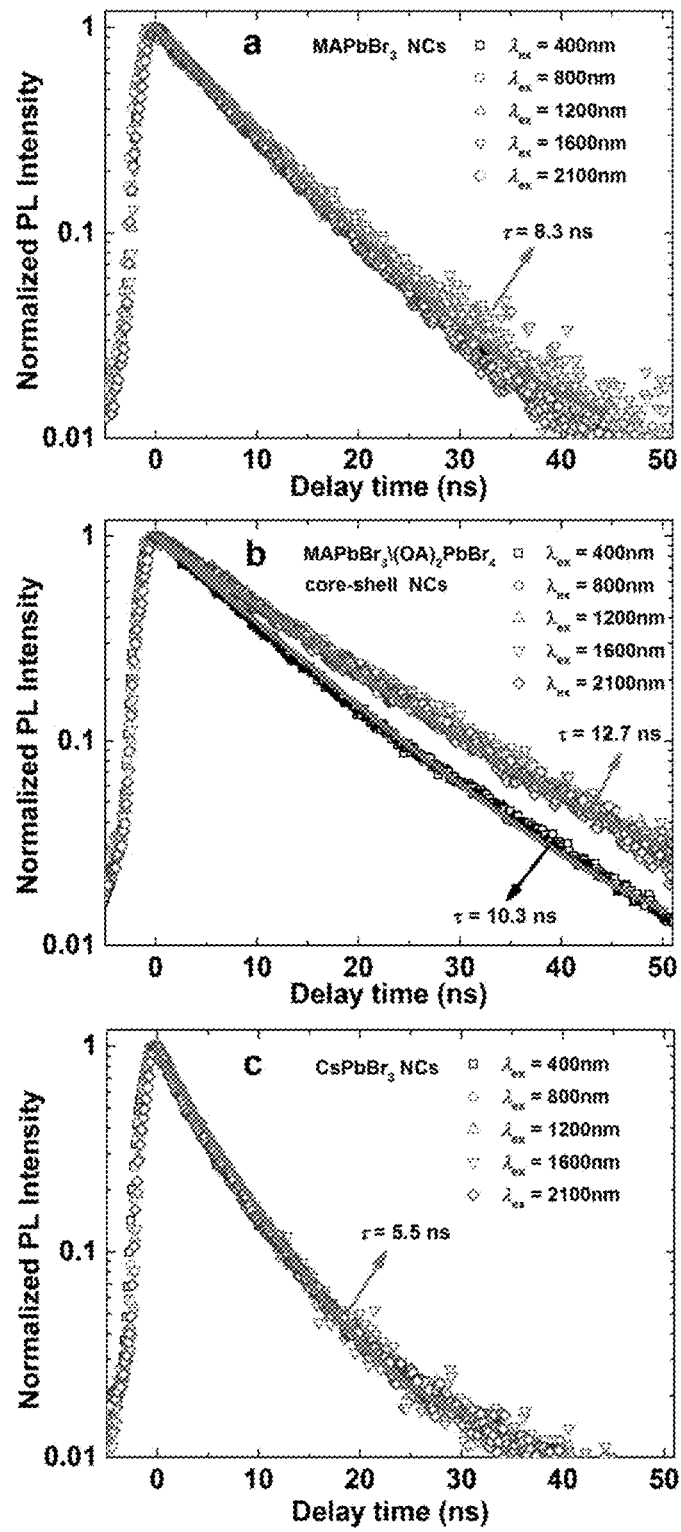

FIG. 28 shows a comparison between the PL decay traces of the MAPbBr$_3$, MAPbBr$_3$/(OA)$_2$PbBr$_4$ and CsPbBr$_3$ NCs under one-, two-, three-, four- and five-photon excitation at 400, 800, 1200, 1600, and 2100 nm, respectively. (a) One- and multi-photon excited PL decay curves in MAPbBr$_3$ NCs; (b) Longer one- and multi-photon excited PL decay lifetimes are obtained for MAPbBr$_3$/(OA)$_2$PbBr$_4$ NCs than for MAPbBr$_3$ NCs; (c) Shorter PL decay lifetimes in CsPbBr$_3$ NCs under one- and multi-photon excitation.

Figure 29:
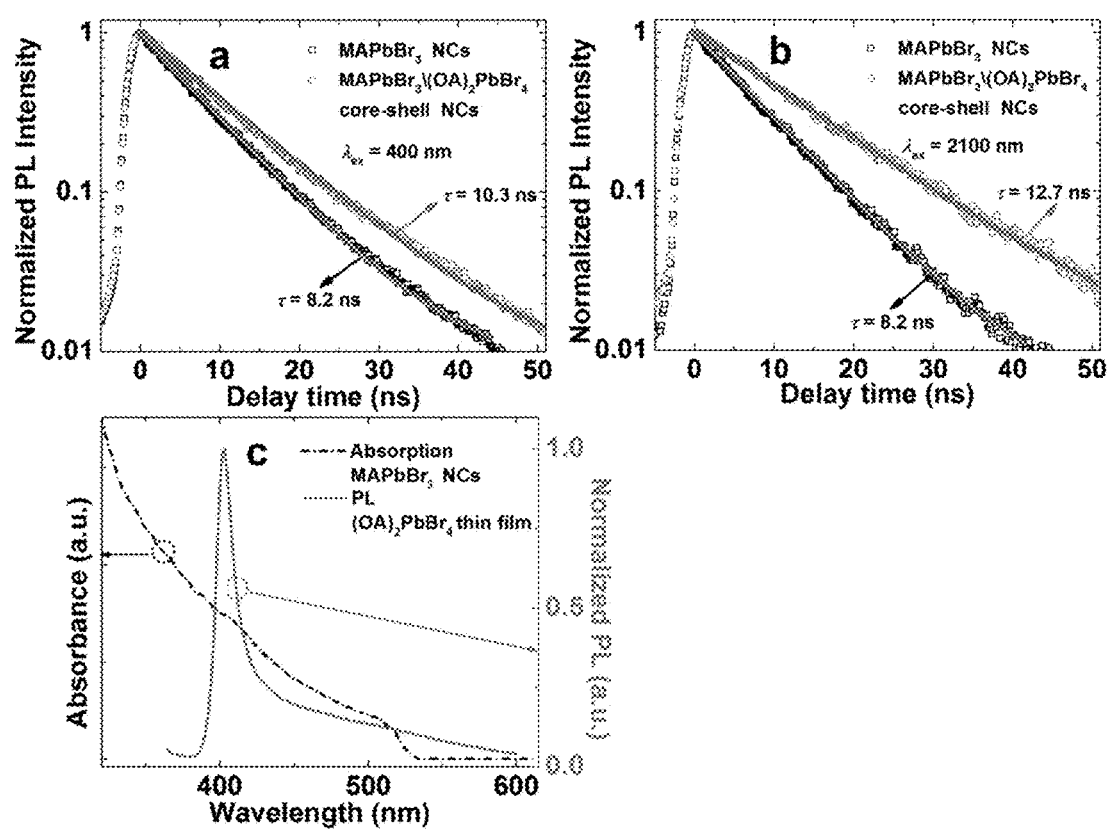

FIG. 29 shows a comparison between the PL decay traces of the MAPbBr$_3$ and MAPbBr$_3$/(OA)$_2$PbBr$_4$ NCs and the spectral overlap between shell emission and core absorption (a) Comparison between PL decay curves from MAPbBr$_3$ and MAPbBr$_3$/(OA)$_2$PbBr$_4$ NCs under one-photon excitation; (b) Longer five-photon excited PL lifetime of core-shell MAPbBr$_3$/(OA)$_2$PbBr$_4$ NCs as compared to the core-only MAPbBr$_3$ NCs. (c) Large spectral overlap between the emission of (OA)$_2$PbBr$_4$ thin film and the excitation of MAPbBr$_3$ NCs.

Figure 30:
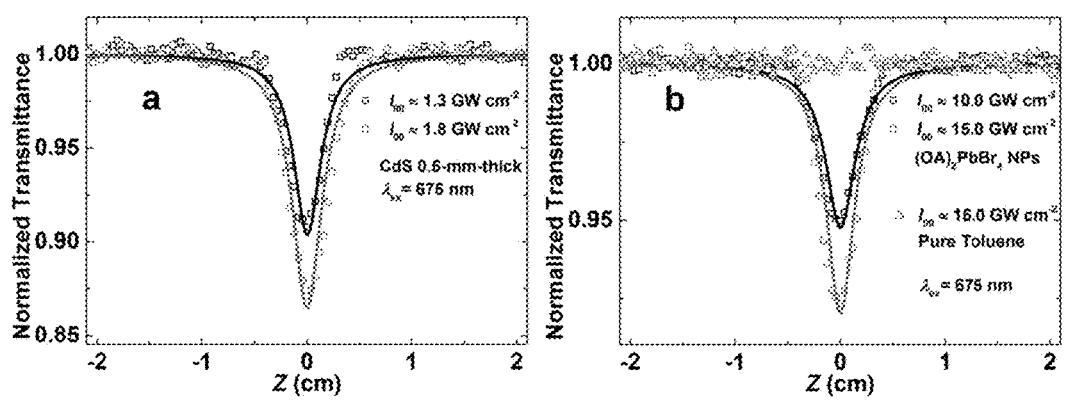

FIG. 30 shows open-aperture Z-scan measurements on (OA)$_2$PbBr$_4$ nanocrystals (a) Open-aperture Z-scan curves of the standard sample CdS (0.5-mm thick) at 675 nm with peak excitation intensities of ~1.3 and ~1.8 GW cm$^{-2}$; (b) Open-aperture Z-scan responses from the toluene solutions of (OA)$_2$PbBr$_4$ nanocrystals (unknown concentration), contained in 1-mm-thick cuvette under laser excitation at 675 nm and with peak intensities of ~10.0 and ~15.0 GW cm$^{-2}$. The almost flat open-aperture Z-scan curve of the toluene under the same excitation condition (contained in 1-mm-thick cuvette, laser excitation at 675 nm with peak intensity of ~15.0 GW cm$^{-2}$) is also shown in (b).

DESCRIPTION

The disclosure presents the utilization of core-shell type organic-inorganic perovskite nanocrystals with different sizes and shapes for applications in optical limiting, multiphoton excited upconversion PL and lasing. As an example, CH$_3$NH$_3$PbBr$_3$ (MAPbBr$_3$) single crystals have demonstrated relatively large two-photon absorption coefficients. Its corresponding nanocrystals have also shown high photoluminescence quantum yield (PLQY), tunable bandgap and PL wavelengths. Accordingly, in a first aspect, the present disclosure provides a nanocrystal comprising a core comprised in a shell, wherein the core comprises a first material of a perovskite structure comprising, or essentially consisting of, a first, small organic cation not exceeding a molar weight of about 45 g/mol, a first, divalent metal and a first counter anion, and wherein the shell comprises a second material of a perovskite structure comprising, or essentially consisting of, a second, large organic cation having a molar weight between about 74 g/mol and about 187 g/mol, optionally the first organic cation, a second divalent metal and a second counter anion. In this context, 'nanocrystal' refers to a nanometer-scale crystalline particle. The nanocrystal is provided as a 'core-shell' nanocrystal, which refers to a 3-dimensional core enclosed in a substantially 2-dimensional shell. The core may be encapsulated in the shell. The crystal structures in the core may differ from the crystal structures in the shell. However, both crystal structures may be in an inorganic-organic perovskite modification.

An inorganic-organic 'perovskite' refers to a modification wherein the elements are arranged in a cubic structure with the general formula of AMX$_3$. In this structure, an A-site ion, is on the corners of the lattice. M site ions, on the center of the lattice, could be 3d, 4d, and 5d transition metal elements. Crystals of perovskite appear as cubes, but are pseudocubic and crystallize in the orthorhombic system. Perovskites may be structured in layers, with the above AMX$_3$ structure separated by thin sheets of intrusive material.

The first 'core' material may comprise a first 'small organic cation'. The first small organic cation may occupy the A-site of the formula AMX$_3$ described above. This may result in an inorganic-organic perovskite structure. The first, small organic cation may be any organic moiety with a molecular weight not exceeding 45 g/mol. It may further include a cationic functional group, which may include an ammonium cation.

The first 'core' material may further comprise a first 'divalent metal'. The first divalent metal may occupy the M-site of the formula AMX$_3$ described above. 'Divalent metal' in this context refers to any metal which may form the perovskite structure as described above. Notably, the divalent metal may be selected from the group consisting of transition metals, lanthanoids, post-transition metals and heavy metals. 'Divalent' refers to the metal being present in the oxidation state +II.

The first 'core' material may further comprise a first 'counter anion'. The first counter anion may be selected from any anion which may form the perovskite structure as described above. Preferably, the weight of one counter anion may not exceed about 100 g/mol. More preferably, the counter anion is selected from the group of the non-metals. More preferably, the counter anion is selected from the group of the halogens. The disclosure may refer to a first or a second counter anion at several sections and for several functions, wherein each may be the same or they may be different from each other.

Within the core of the core-shell nanocrystal, the elements may be arranged in a 3-dimensional network. This network may be arranged in a crystalline modification. The crystalline modification may be a perovskite modification. Further, it may be in a cubic arrangement.

The second 'shell' material may be substantially 2-dimensional. In the second shell material, parts or all of the first small organic cation may be replaced by a second, large organic cation, thereby breaking the cubic symmetry. In the second shell material, a layered structure as described above may be present, wherein the above AMX$_3$ structure is separated by thin sheets of intrusive material, the intrusive material being the second, large cation. The number of layers may be described with the integer 'n'. The second, larger cations may lead to a larger d-spacing of the divalent metal atoms to their counter anions, which influences the optical properties as well as the stability of the ensuing nanocrystal.

The second shell material may additionally comprise a second divalent metal and a second counter anion, which may be described as the first divalent metal and the first counter anion. The specific divalent metal and counter anion used in the shell may differ from those used in the core. Alternatively, they may be the same.

The second 'shell' material may additionally comprise residues of the first, smaller organic cation. The core material may additionally comprise residues of the second, larger organic cation.

Advantageously, by keeping within the weight ranges of the first, smaller organic cation and the second, larger organic cation, the perovskite modification is tuned to an optimal ratio, leading to the observed core-shell configuration. By controlling the weight range of the organic cations, the unique properties of the nanocrystals with regard to optical limiting, multiphoton excited upconversion PL and lasing can be obtained.

To further explain the above, in order to form a 3D core perovskite material, only small organic cations that fit in the cuboctahedral cavity of the metal-counter anion octahedra can be used. This cation selection is limited only to those cations with molar weight of about 32 to 45 g/mol. With respect to the second organic cation (from the shell material), sizes may range from molar weights of 74 to 187 g/mol. Organic cations of lower weight (shorter chain), e.g. $C_2$-$C_3$-Alkyls, may yield an unstable product, hence it cannot be used for shell formation. Similarly, organic cations of higher weight than 187 g/mol (longer chain, $C_{13}$ and longer) may face difficulties forming a 2D shell material concomitantly to 3D core formation during coprecipitation, due to slower reaction/formation kinetics.

The term 'any organic moiety' as used herein refers to carbon-containing moieties. These moieties can be linear or branched, substituted or unsubstituted, and are derived from hydrocarbons, typically by substitution of one or more carbon atoms by other atoms, such as oxygen, nitrogen, sulfur, phosphorous, or functional groups that contain oxygen, nitrogen, sulfur, phosphorous. The organic moiety can comprise any number of carbon atoms, but preferably it is a low molecular weight organic moiety. It is preferred that the organic moiety is compatible with the reaction described herein and does not adversely affect the described formation of nanocrystals. Suitable groups and moieties are well known to those skilled in the art or can be readily identified by routine experimentation.

In a preferred embodiment, the organic moiety can be a linear or branched, substituted or unsubstituted alkyl with 1 to x carbon atoms; linear or branched, substituted or unsubstituted alkenyl with 2 to x carbon atoms; linear or branched, substituted or unsubstituted alkinyl with 2 to x carbon atoms; linear or branched, substituted or unsubstituted alkoxy with 1 to x carbon atoms; substituted or unsubstituted cycloalkyl with 3 to x carbon atoms; substituted or unsubstituted cycloalkenyl with 3 to x carbon atoms; substituted or unsubstituted aryl with 6 to x carbon atoms; and substituted or unsubstituted heteroaryl with 3 to x carbon atoms; with x being any integer of 2 or more, depending on the weight range as indicated above.

In a further embodiment of the present disclosure, the organic moiety can be a linear or branched, substituted or unsubstituted alkyl with 1 to 11 carbon atoms; linear or branched, substituted or unsubstituted alkenyl with 3 to 11 carbon atoms; linear or branched, substituted or unsubstituted alkoxy with 1 to 11 carbon atoms, substituted or unsubstituted cycloalkyl with 5 to 11 carbon atoms; substituted or unsubstituted cycloalkenyl with 5 to 11 carbon atoms; substituted or unsubstituted aryl with 5 to 11 carbon atoms; and substituted or unsubstituted heteroaryl with 5 to 11 carbon atoms, depending on the weight range as indicated above.

The organic moiety can also be a combination of any of the above-defined groups, including but not limited to alkylaryl, arylalkyl, alkyl heteroaryl and the like, to name only a few, all of which may be substituted or unsubstituted.

The term "substituted" as used herein in relation to the above moieties refers to a substituent other than hydrogen. Such a substituted is preferably selected from the group consisting of halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, —OR, —NRR', —NR, —C(O)R, —C(O)OR, —(CO)NRR', —NR'C(O)R, —OC(O)R, aryl with 5 to 10 carbon atoms, cycloalk(en)yl with 3 to 10 carbon atoms, 3- to 8-membered heterocycloalk(en)yl, and 5- to 10-membered heteroaryl, wherein R and R' are independently selected from hydrogen, alkyl with 1 to 10 carbon atoms, alkenyl with 2 to 10 carbon atoms, alkynyl with 2 to 10 carbon atoms, aryl with 5 to 10 carbon atoms, cycloalk(en)yl with 3 to 10 carbon atoms, 5- to 10-membered heteroaryl, comprising 1 to 4 heteroatoms selected from nitrogen, oxygen, and sulfur, and 5- to 10-membered heterocycloalk(en)yl, comprising 1 to 4 heteroatoms selected from nitrogen, oxygen, and sulfur. Any of these substituents may again be substituted, it is however preferred that these substituents are unsubstituted.

Alkyl, or abbreviated 'alk', refers to a saturated hydrocarbon moiety, such as methyl, ethyl, and the like. Alkenyl and Alkynyl comprise at least one carbon-carbon double bonds or triple bonds, respectively, and are otherwise defined as alkyl above.

Cycloalkyl refers to a non-aromatic carbocyclic moiety, such as cyclopentanyl, cyclohexanyl, and the like.

Cycloalkenyl refers to non-aromatic carbocyclic compounds that comprise at least one C—C double bond.

Similarly, heterocycloalk(en)yl relates to cycloalk(en)yl groups wherein 1 or more ring carbon atoms are replaced by heteroatoms, preferably selected from nitrogen, oxygen, and sulfur.

Aryl relates to an aromatic ring that is preferably monocyclic. Preferred aryl substituents are moieties with 6 carbon atoms, such as phenyl.

Heteroaryl refers to aromatic moieties that correspond to the respective aryl moiety wherein one or more ring carbon atoms have been replaced by heteroatoms, such as nitrogen, oxygen, and sulfur.

All of the afore-mentioned groups can be substituted or unsubstituted. When substituted, the substituent can be selected from the above list of substituents.

The term 'at least one' as used herein relates to one or more, for example 1, 2, 3, 4, 5, 6, 7, 8, 9 or more of the referenced species.

Halogen as used herein refers to F, Cl, Br, and I.

The small organic cation and the large organic cation core-shell nanocrystal may each comprise a cationic functional group. This cationic functional group may serve as the counter ion in the perovskite structure. The cationic functional group may be any functional group which possesses a positive charge and is stable under the reaction conditions which result in the nanocrystal. In some embodiments, the cationic functional group may be an ammonium ion. The ammonium ion may be a primary, a secondary, a tertiary or a quaternary ammonium ion. The ammonium may be substituted with the organic moiety. Depending on whether the cationic functional group is a primary, a secondary, a tertiary or a quaternary ammonium ion, the small organic cation and the large organic cation may comprise one, two, three or four organic moieties.

In some embodiments, the organic moiety may be at least one alkyl moiety. The alkyl moiety may be branched or linear. In some embodiments, the at least one alkyl moiety may be at least one linear alkyl moiety.

In some embodiments of the first organic cation, the organic moiety may be a substituted alkyl moiety. In particular, the alkyl moiety may be substituted with a nitrogen functionality. In one example, the organic moiety may be an imine. The resulting first organic cation would therefore be a formamidinium cation.

In the core-shell nanocrystal, the first material of the core may comprise, or may essentially consist of, material of the general formula $(S-NH_3)MX_3$ and the shell may comprise, or may essentially consist of, a second material of the general formula $(C_{4-12}\text{-Alk-}NH_3)_2(S-NH_3)_{n-1}M_nX_{3n+1}$ wherein
S is $-CH_3$ or $-CH=NH$;
n is an integer selected from 1 to 4;
M is a divalent metal; and
X is a counter anion,
wherein M and X of the core and M and X of the shell may be the same or different.

In this embodiment, the first, small organic cation is described as $S-NH_3$ and the second, large organic cation is described as $C_{4-12}\text{-Alk-}NH_3$. The molecular weight limitation is determined through the sizes of the organic moieties within the formula. Hence, the first, small organic cation may comprise a primary ammonium cation and an optionally substituted methyl, wherein the substitution may be another nitrogen functionality. In one example, the first, small organic cation is methyl ammonium. Alternatively, it may be a formamidinium cation. The second, large organic cation may comprise a primary ammonium cation and a butyl, pentyl, hexyl, heptyl, octyl, nonyl, decyl, undecyl or dodecyl moiety. In one example, the second, large organic cation is octyl ammonium. 'n' signifies the number of layers within the shell structure with n=1 being a pure 2-dimensional layer and n=2-4 being a quasi-2-dimensional layered structure ('substantially 2-dimensional'). In one example, 'n' is 2.

In some embodiments, it may be desired to stabilize the nanocrystal by additionally providing at least one alkoxysilane to each of the first, small and the second, large organic cation. Advantageously, this may allow for sol-gel reactions which may further increase the stability of the nanocrystals. In one example, the alkoxysilane is 3-aminopropyltriethoxysilane (APTES).

As mentioned previously, the second, large organic cation in the shell material may separate the metal from the counter ion, thereby increasing the d-spacing. An increased d-spacing within the shell has the advantage of altering the optical properties, resulting in the unique optical nonlinear properties which are observed in the present disclosure.

The first and second counter anion may be a halogen, preferably selected from the group consisting of fluoride, chloride, bromide and iodide. In one example, the counter anion is bromide.

The first and second divalent metal in the core-shell nanocrystal may be a heavy metal. Heavy metals may be associated with a higher density and a lower reactivity than other (light) metals. As such, the divalent heavy metal may be selected from zinc, mercury, lead, iron, copper, tin, silver, gold, platinum, gallium, thallium, hafnium, cobalt, ruthenium and indium. In one example, the divalent metal is lead.

Additionally or alternatively, the first and/or second divalent metal in the core-shell nanocrystal may be a post-transition metal. Post-transition metals may refer to the metallic elements in the periodic table located between the transition metals (to their left) and the metalloids (to their right). These elements may include gallium, indium thallium, tin, lead, bismuth, cadmium, mercury and aluminum. In one example, the divalent metal is lead.

The nanocrystal of the present disclosure may be in a spherical. This may be seen in contrast to a cubic shape. The diameter of the nanocrystal may be about 1-50 nm, preferably 5-30 nm, more preferably 5-20 nm, or approximately about 8-15 nm.

The photoluminescence quantum yield of the nanocrystal may be higher than 50% one month after synthesis. Additionally or alternatively, it may be higher than 10% two months after synthesis. Photoluminescence quantum yield (PLQY) is usually measured by two methods. One method is called relative PLQY, which is measured by comparing with reference sample. Another method is called absolute PLQY, which is measured with integrating sphere. The PLQY of the NCs in the present application is measured with integrating sphere and is absolute PLQY. This method does not depend on reference sample and its concentration. Absolute PLQY measurement is more reproducible compared to relative PLQY because there is no variable and constraints are fixed all time. After 2 months, the PLQY measured is accurate too.

In one embodiment, the core-shell nanocrystal may be further encapsulated with $SiO_x$ and/or $SiO_2$. The silicon oxide may be utilized as an additional shell or as a medium to embed several nanoparticles. In another embodiment, the core-shell nanocrystal may be further encapsulated with solid lipid structures. Here, the term 'lipid' should be used in a broad sense of materials, such as long-chain saturated fatty acids (e.g. stearic acid), mono- di- and triglycerides, copolymer micelles, nonionic ABC triblock copolymers composed of a central hydrophobic chain (B) surrounded by hydrophilic moieties (A and C), steroids, waxes, or mixtures of the aforementioned. Furthermore, the core and core-shell nanocrystals may be further encapsulated in the voids of porous metal-organic frameworks, such as $Cu_3(1,3,5\text{-benzene tricarboxylate})_2$ (HKUST-1), $Zn_4O$ nodes with 1,4-benzodicarboxylic acid struts (IRMOF-1), other IRMOF series (like IRMOF-10 and IRMOF-16), zinc ions coordinated by four imidazolate rings (ZIF-8), UiO-66 made up of $[Zr_6O_4(OH)_4]$ clusters with 1,4-benzodicarboxylic acid struts, etc. to enhance the multiphoton absorption property and improve stability and biocompatibility.

Hence, in a second aspect, there is provided a matrix having a nanocrystal as described above encapsulated therein. The matrix material may be any material listed above, notably it may be a solid material. It may be an inorganic or an organic material, or a combination thereof. The inorganic matrix material may be selected from silica, for example $SiO_2$ and/or $SiO_x$. The organic matrix material may be selected from lipids. Where the matrix is a combination of an inorganic and an organic material, this may be a 'metal-organic framework' (MOF). Advantageously, the nanocrystal is embedded in the voids of the matrix material. This may be beneficial in relation with stability and/or cytotoxicity of the nanocrystal.

In a third aspect, the present disclosure provides a process for the synthesis of a nanocrystal comprising a core comprised in a shell, the process comprising a) preparing a precursor solution containing a first and a second divalent metal, a first organic cation not exceeding a molar weight of about 45 g/mol, a second organic cation having a molar weight between about 74 g/mol and about 187 g/mol, and a first and second counter anion in a polar aprotic solvent; and b) subjecting the precursor solution to a non-polar solvent to form the nanocrystal comprising a core comprised in a shell. The formation of the core-shell nanocrystal may occur in a 'one-pot'-approach, as the precursor solution is mixed into non-polar solvent without any distinction of a process part relating to the 'core' and a process part relating to the 'shell'. Surprisingly, it has been found that the process resulting in a core-shell nanocrystal provides optimal results when the core-shell nanocrystal is produced in a 'one-pot' approach. An alternative process wherein the core was produced in a first step and the shell was envisaged to be produced in a second step, was proven to be unsuccessful.

The polar aprotic solvent may be selected from the group consisting of tetrahydrofuran, ethyl acetate, acetone, N,N-dimethylformamide, acetonitrile, dimethyl sulfoxide, nitromethane and propylene carbonate, and mixtures thereof. In one example, the polar aprotic solvent is N,N-dimethylformamide (DMF).

The non-polar solvent may be selected from the group consisting of hexane, benzene, toluene, diethyl ether, chloroform, 1,4-dioxane, and mixtures thereof. In one example, non-polar solvent is toluene.

The molar ratio of the first, small organic cation to the second, large organic cation may be varied in the range of 9:1 to 1:9. Optimal results regarding optical properties may be obtained by a ratio wherein the first, small organic cation is predominantly present (i.e. in more than 50 mol %).

In one embodiment, step b) of the process as described above may proceed at elevated temperature, such as between 40-200° C., preferably at between 50-100° C., more preferably at about 60° C.

In a fourth aspect, there is provided use of the nanocrystal comprising a core comprised in a shell as described above for optical limiting, bioimaging and upconversion lasing application.

Figure 1:
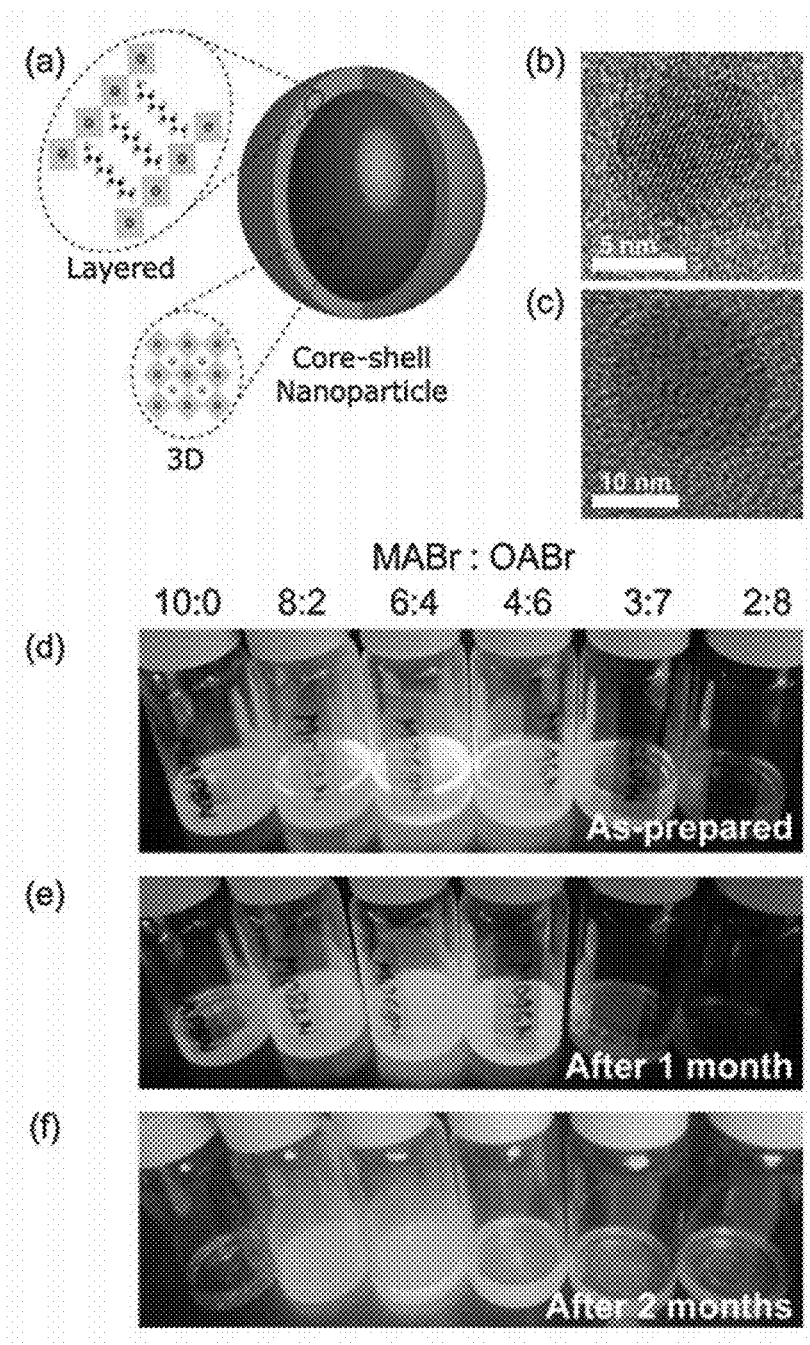
FIG. 1 shows (a) a schematic illustration of the core-shell type nanocrystal. (b-c) TEM image of the MAPbBr$_3$-(OA)$_2$PbBr$_4$ core-shell type nanoparticle with MABr and OABr in a molar ratio of 8:2 and 3:7. (d-f) Photographic images of mixed organolead bromide perovskite nanocrystals with different MABr-OABr ratios in toluene solution under UV exposure over different time intervals.

One of the methods to enhance the stability, efficiency and brightness of semiconductor nanocrystals is by growing a shell of a larger band-gap semiconductor around it. Such nanocrystals with small regions of one material embedded in another with a wider band gap are known as core-shell semiconducting nanocrystals (CSSNCs). This type of crystal engineering improves the quantum yield of the nanocrystals by confining charge carriers, passivating non-radiative recombination sites and making them more robust to processing conditions. In a bid to explore the same advantages in perovskite nanocrystals, this disclosure investigated the possibility of developing nanocrystals comprising of a high band-gap 2D perovskite shell over a low band-gap perovskite core as shown in FIG. 1 a.

The LARP method was adopted for the synthesis. A first, small organic cation, a metal salt, capping agents like oleylamine and oleic acid were dissolved in DMF in an appropriate molar ratio to make the final precursor solution for the nanocrystals (Examples). While in this results section lead bromide as a first and second divalent metal with first and second counter anion, methylammonium as a first small organic cation and octylammonium as a second large cation was utilized, the results should not be understood to be limited to these compounds.

This precursor solution was then swiftly injected into toluene kept at elevated temperature and stirred vigorously to form the core nanocrystals. The mixture was then centrifuged and the supernatant containing the nanocrystals was collected for further studies. For the synthesis of the mixed cations, for example methylammonium-octylammonium (MA-OA) lead bromide nanocrystals, MABr and OABr at 8:2, 6:4, 4:6, 3:7 and 2:8 molar ratios were used in the precursor solution such that the total amount of organic ammonium bromide and synthesis conditions are constant for all combinations. The structural characterization of the nanocrystals thus prepared were done using transmission electron microscopy (TEM) and X-ray powder diffraction (XRD) and their photophysical properties were evaluated by recording their optical absorption, photoluminescence (PL) and time resolved photoluminescence spectra.

FIGS. 1b and c show representative TEM images of spherical mixed organo-lead bromide nanocrystals obtained from cation ratios 8:2 and 3:7 (see the Examples for all combinations of cations). The nanocrystals seem to be spherical with an average diameter of 5-12 nm. There is no signature of the formation of 3D bulk crystals or platelets. This may be due to the influence of the oleylamine used as a capping ligand in this synthesis which controls the growth and crystallization of nanocrystals whereas oleic acid prevents nanocrystals from self-aggregation and at the same time contributes to the colloidal stability. No significant size change was observed for the particles obtained with cation ratios 8:2 and 6:4 (particle size ~5 nm) whereas synthesis with cation ratios 3:7 and 2:8 afforded nanocrystals with a particle size of around 12 nm. The as-synthesized particles showed bright luminescence under UV light (FIG. 1d-f). Remarkably, the luminescence of certain compositions (stored under ambient conditions, at 60% relative humidity (RH)) remained stable for 2 months. Specifically, the mixed compositions within a limited MABr:OABr range remained highly luminescent. This indicated the possible advantages brought about by the core-shell architectures and motivated further analysis.

Figure 4:
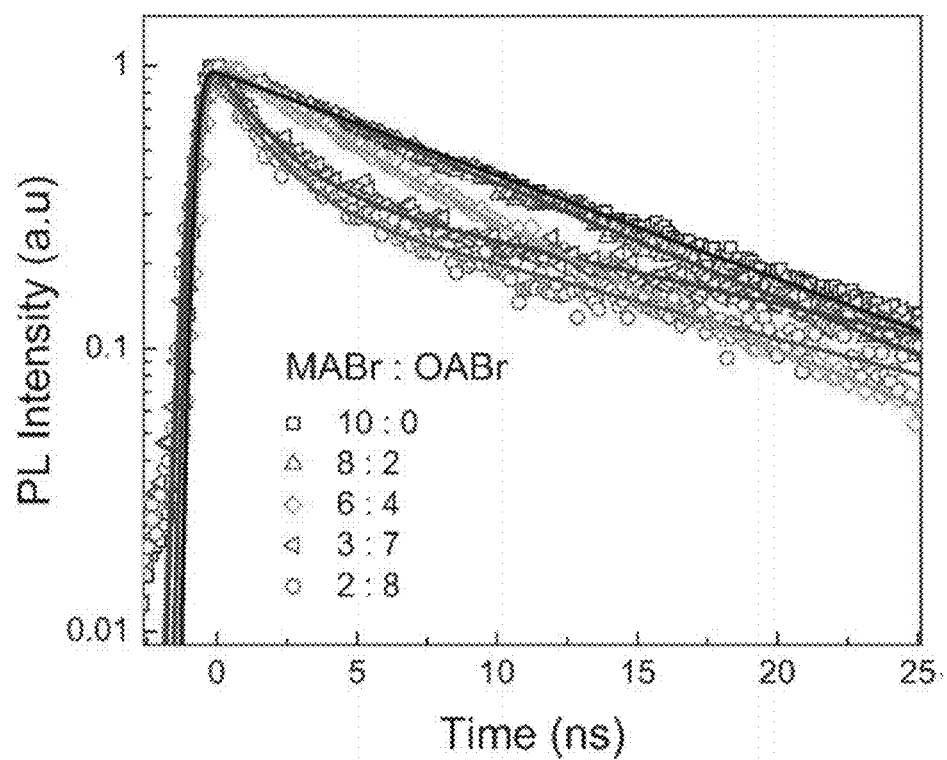
FIG. 4 show the time-resolved PL decay and fitted curves for mixed organolead bromide perovskite nanocrystals in solution extracted at their dominant emission peaks (as shown in brackets) following excitation at 400 nm (1 kHz, 150 fs, 0.2 mJ cm$^{-2}$). Solid lines are fitted curves.
Figure 5:
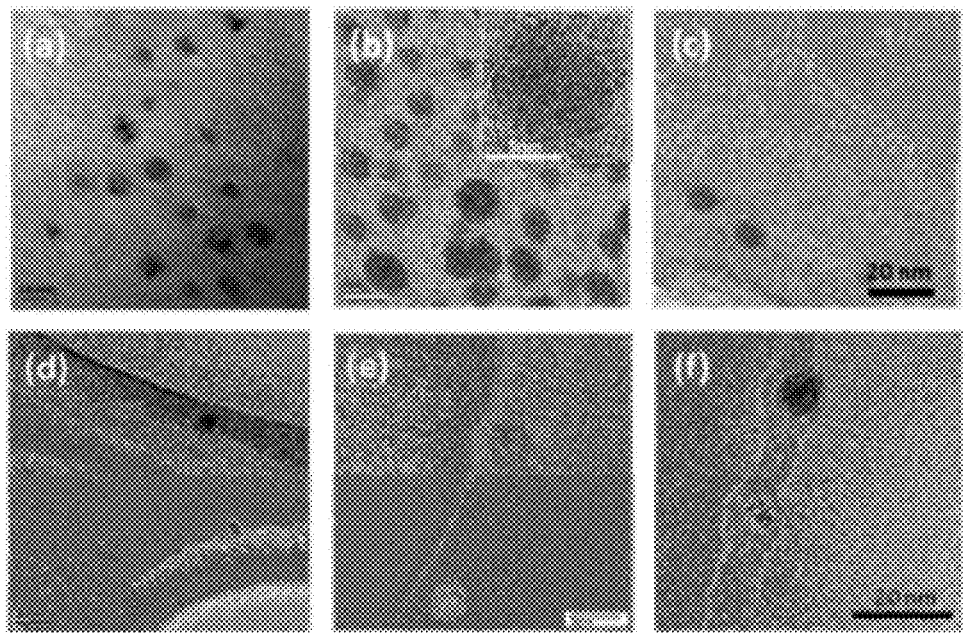
FIG. 5 shows TEM images of mixed organo lead bromide perovskite NPs with different MABr and OABr molar ratio: (a) 10:0, (b) 8:2, (c) 6:4, (d) 4:6, (e) 3:7 and (f) 2:8.
Figure 6:
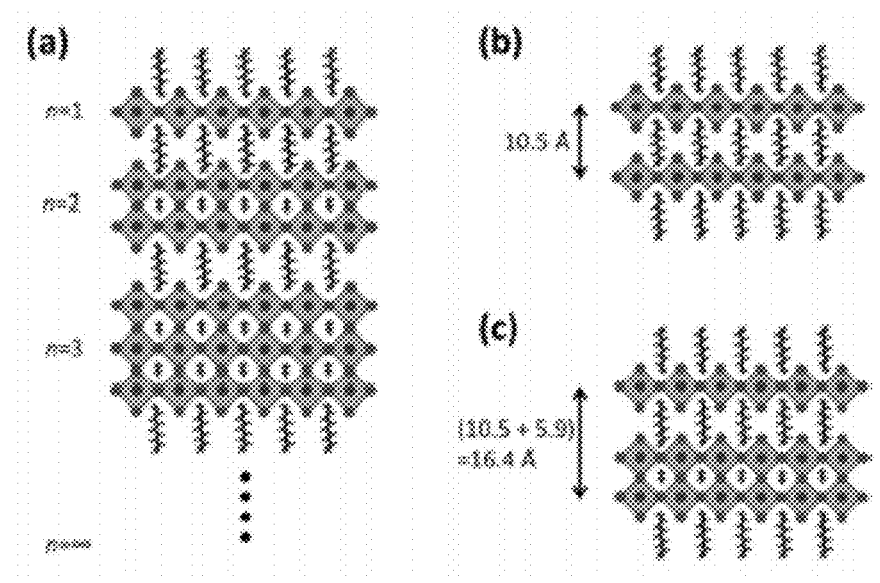
FIG. 6 shows Schematic diagram of perovskite structures with [PbBr$_6$]$_4$— inorganic layer separated by octylamine (a) with different order (n=1, 2, 3, . . . ∞) and (b, c) Perovskite layers with different d-spacing values.
Figure 7:
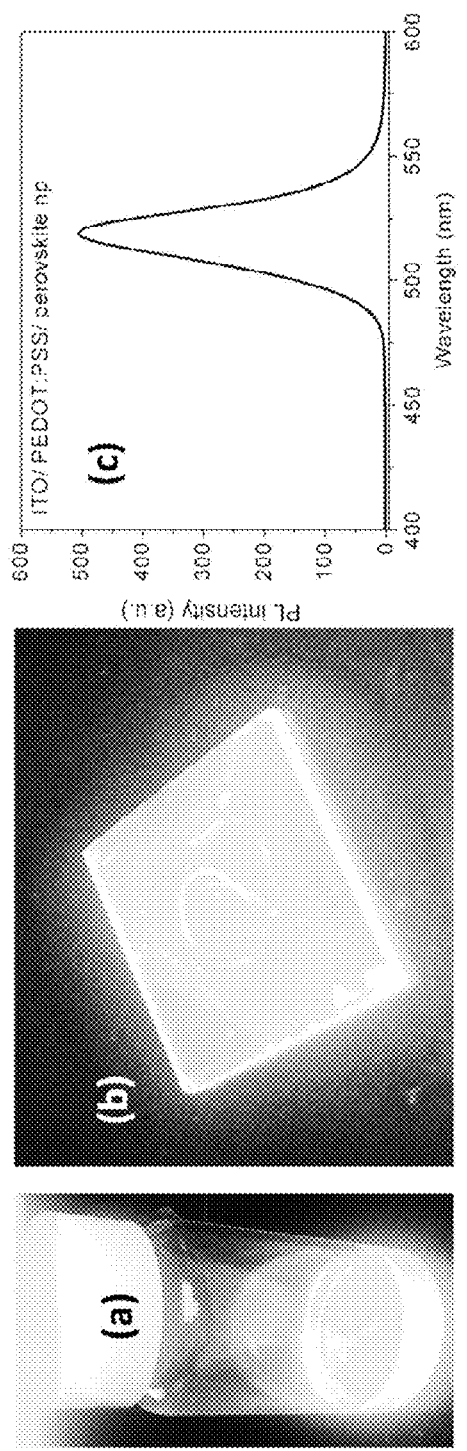
FIG. 7 shows photographs of perovskite nanocrystals under UV-lamp in (a) toluene solution and (b) thin film. (c) Absorbance spectra of perovskite nanocrystals spin-coated on top of ITO/PEDOT:PSS thin film.
Figure 8:
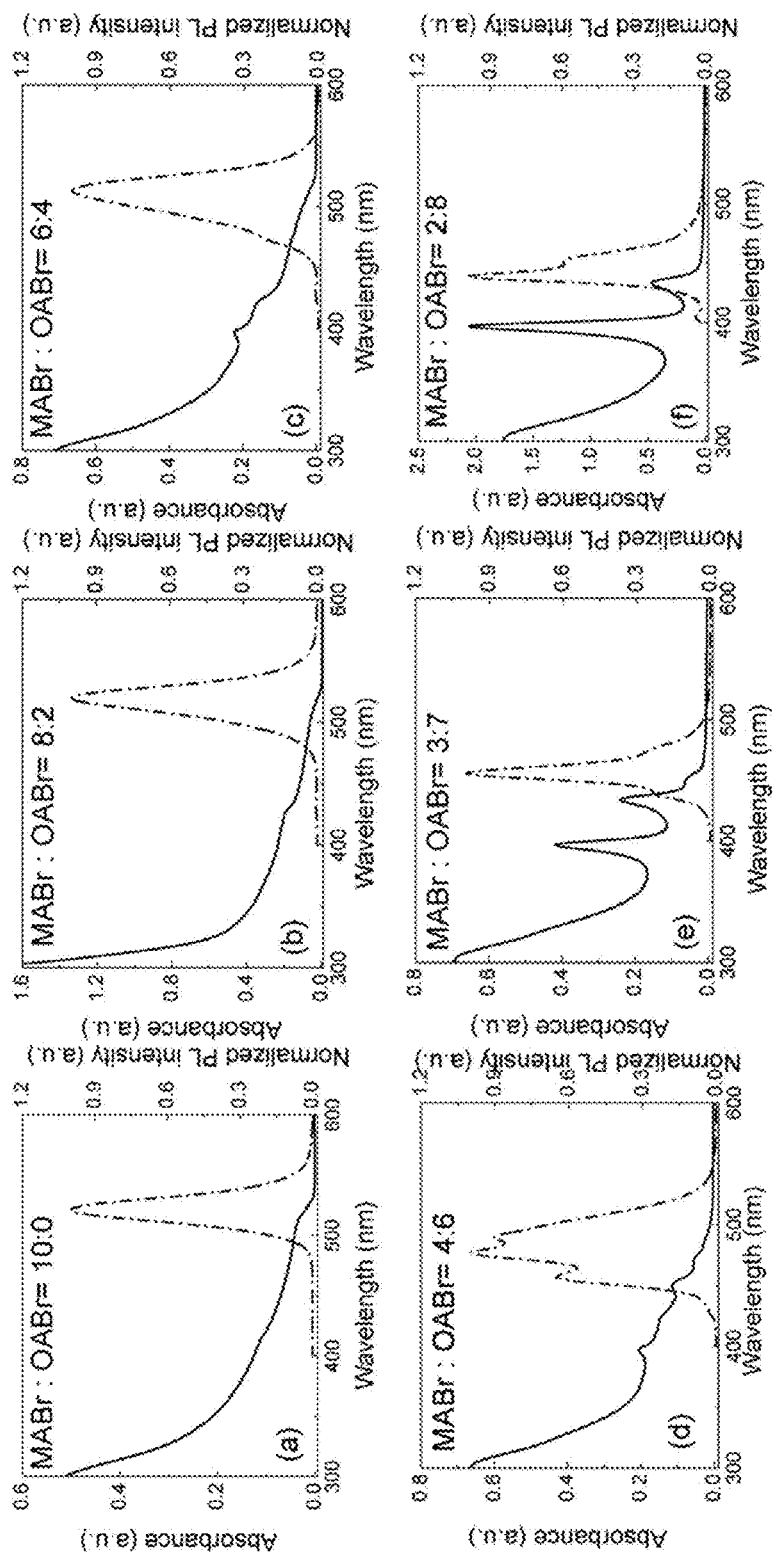
FIG. 8 shows (a-f) UV-vis absorption (solid line) and PL spectra (dotted line) of mixed organo lead bromide perovskite nanocrystals with different molar ratio of MABr with octylamine as the capping ligand.
Figure 9:
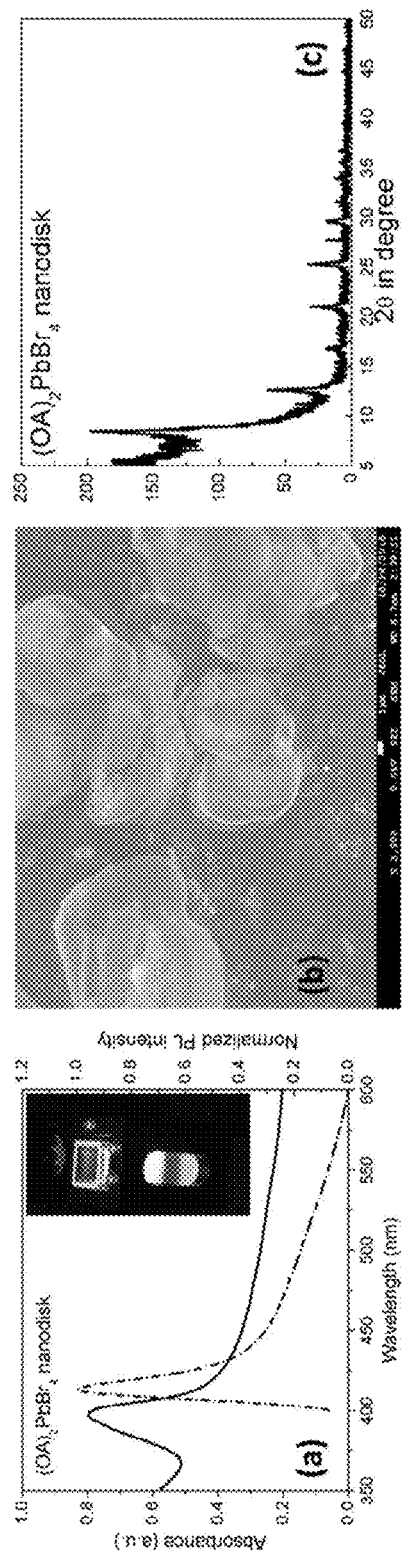
FIG. 9 shows (a) UV-vis absorption (solid line) and PL spectra (dotted line) of (OA)$_2$PbBr$_4$ nanodisks in toluene solutions placed inside the PL spectrofluorophotometer when excited at 350 nm. (b) SEM image and (c) XRD pattern of micrometer sized nanodisks.
Figure 10:
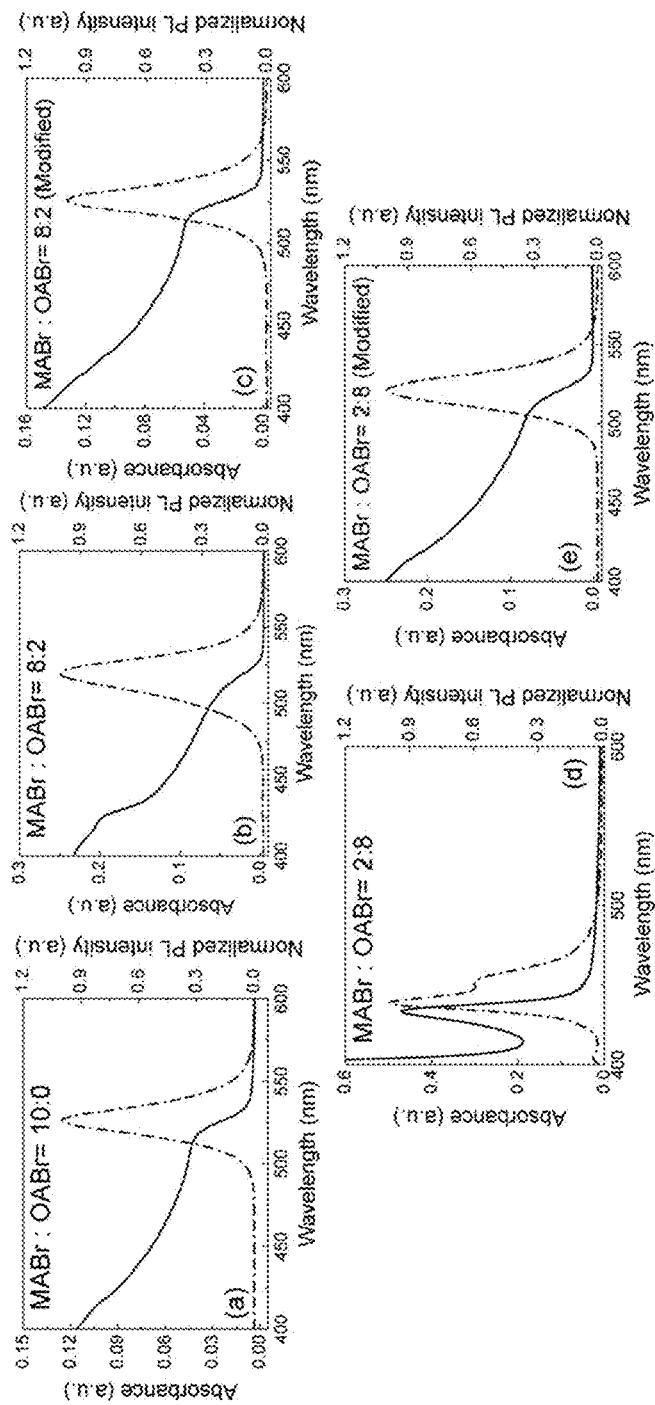
FIG. 10 shows UV-vis absorption and PL spectra of mixed organo lead bromide perovskite nanocrystals with molar ratio of MABr and OABr are (a) 10:0, (b) 8:2, (c) 8:2 (seeded process), (d) 2:8 and (e) 2:8 (seeded process), respectively.
Figure 11:
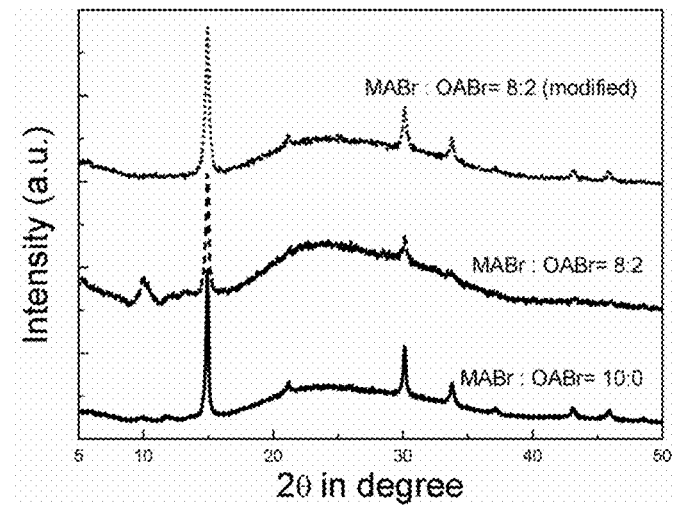
FIG. 11 show an XRD pattern of mixed organo lead bromide perovskite nanocrystals with different MABr and OABr molar ratio as shown in legends. The modified process refers to the seeded synthesis procedure.
Figure 12:
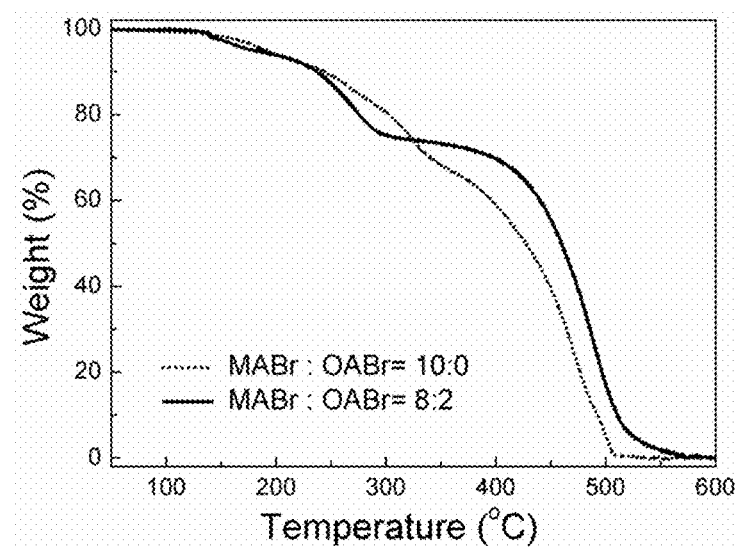
FIG. 12 show the thermogravimetric analysis (TGA) heating curves of mixed organo lead bromide perovskite nanocrystals with molar ratio of MABr and OABr shown in legends.
Figure 13:
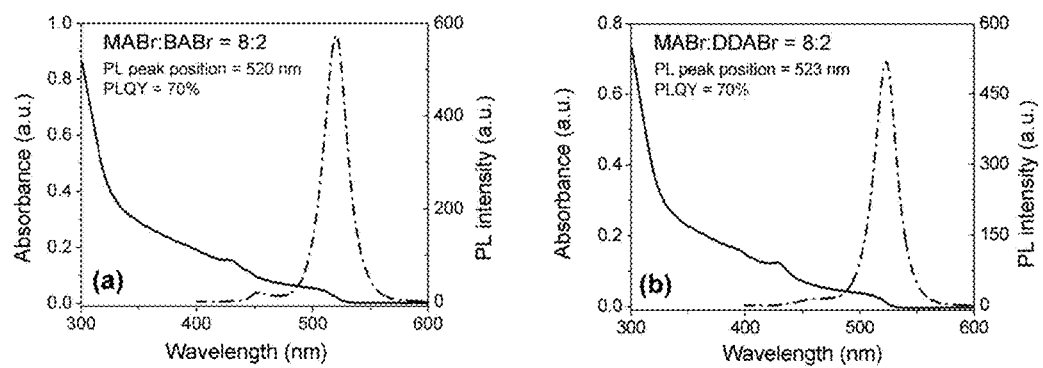
FIG. 13 shows UV-vis absorption and PL spectra of mixed organo lead bromide perovskite nanocrystals with molar ratio of (a) MABr:BABr=8:2 and (b) MABr:DDABr=8:2.

Next, the photophysical properties of these core-shell nanocrystals was evaluated. The optical absorption of the pure $MAPbBr_3$ (n=c) nanocrystals (FIG. 2 a) showed an absorption maximum centered at 513 nm. This absorption peak is blue shifted by 12 nm compared to that reported for the bulk materials (band-gap=2.3 eV or 525 nm). This points to three dimensional confinements in the system possibly due to the formation of nano-sized spherical nanocrystals, such as the $MAPbBr_3$ particles. The absorption shift for precursor solutions with an exemplary OABr content 40% was not significant. Perovskites with a higher OABr concentration displayed a large blue shift for the absorption maxima as well as the formation of additional absorption peaks. For example, perovskite with MABr:OABr=4:6 showed absorption peaks at 397, 433, 450, 471 and 486 nm which are typical for layered perovskites with n=1, 2, 3 or higher order, respectively as shown in FIG. 4. A similar trend is observed for perovskites formed with MABr:OABr=3:7 and 2:8 (see Table 1 in the examples).

Figure 2:
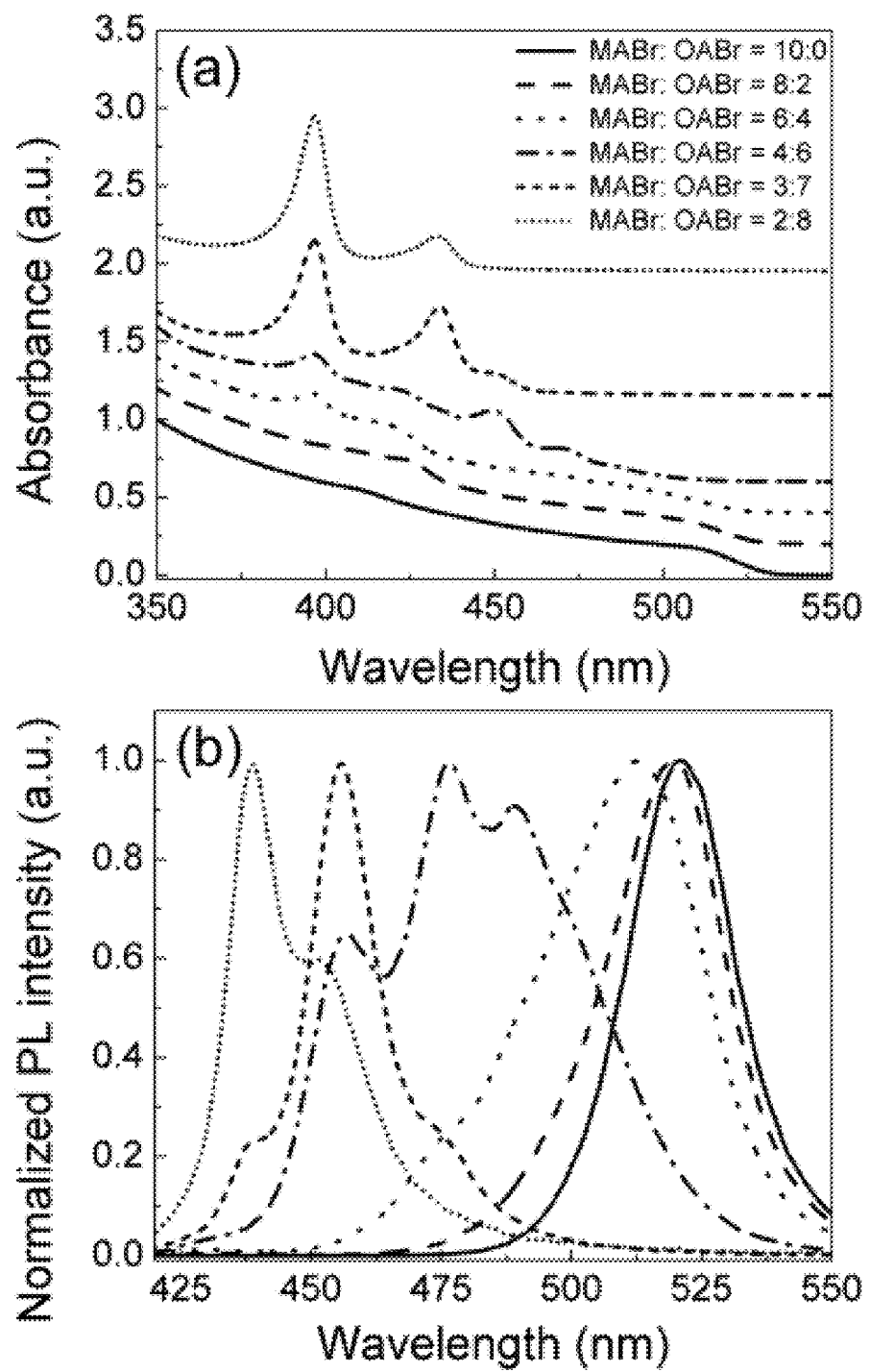
FIG. 2 shows (a) UV-vis absorption and (b) PL spectra of mixed organo-lead bromide perovskite nanocrystals with different molar ratios of MABr and OABr.

Subsequently the photoluminescence properties of these materials were studied. As shown in FIG. 2 b, the nanocrystals, such as $MAPbBr_3$, showed green emission with a PL peak position centered at 521 nm (FWHM=24 nm) and a PLQY of around 80-84%. The mixed cation MABr-OABr (8:2) nanocrystals showed a slight blue shift in the PL peak position (519 nm) with an enhanced PLQY of 92%. This material showed unusual stability in solution in an ambient atmosphere; even after two months the PLQY remains virtually unchanged (see Table 3 in the examples). At a higher MABr:OABr ratio (44:6), similar to the trend observed in the optical absorption, PL peak positions shifted to lower wavelengths and a concurrent decrease in the PLQY was observed (see Table 1 in the examples). In addition, perovskites with MABr:OABr=4:6 and 3:7 showed three PL peak positions, whereas the 2:8 composition showed only two PL peak positions.

Figure 3:
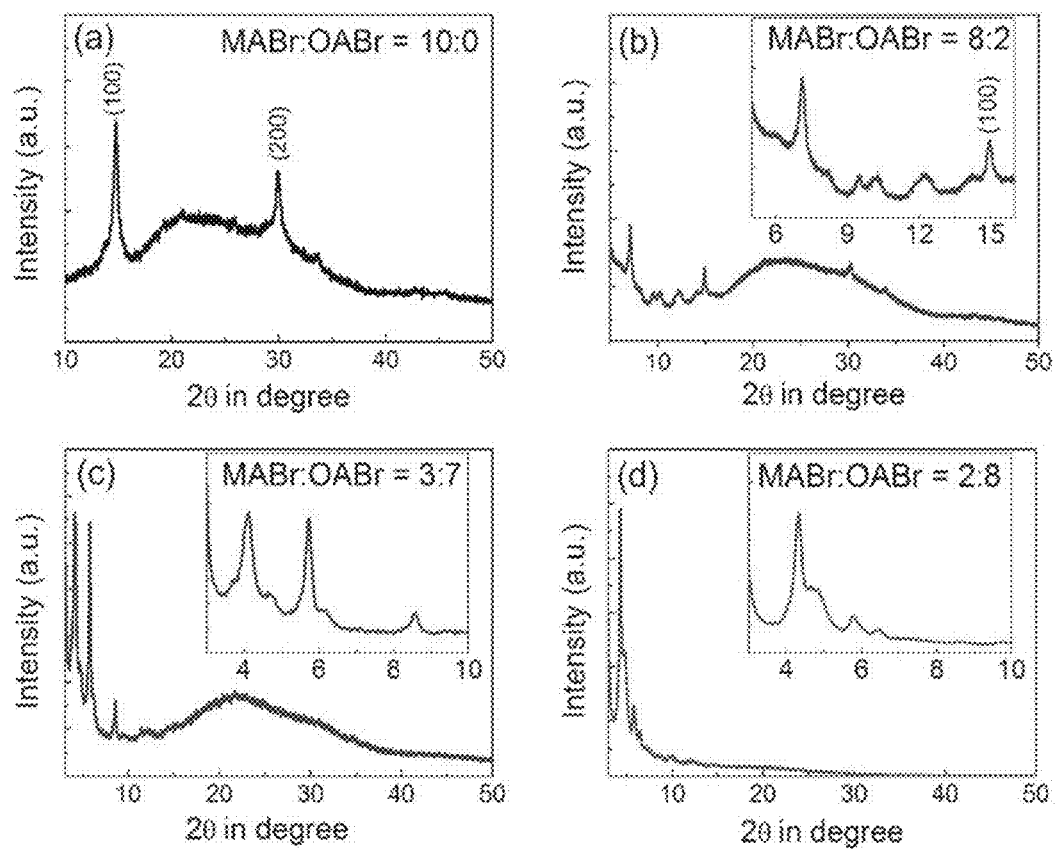
FIG. 3 shows (a-d) XRD pattern of mixed organolead bromide perovskite nanocrystals with different MABr and OABr molar ratios. Inset of (b-d) shows a magnified view of the corresponding XRD pattern.

Generally, the organic-inorganic perovskite structure ($AMX_3$) is formed by a three dimensional network with first, small organic cations occupying the A-site, and the first and/or second divalent metal and halides forming the $MX_6$ octahedra. The peak positions observed for the $MAPbBr_3$ nanocrystals (FIG. 3 a) match well with the patterns reported for bulk crystals, with a d-spacing of 5.9 Å. However, if the second, larger cations (42.6 Å) are introduced, the cubic symmetry is broken; instead layered structures of the general formula $(RNH_3)_2A_{n-1}M_nX_{3n+1}$ (n=1, pure 2D layered; n=∞, 3D structure; and n=defined integer, quasi-2D layered structure) are formed. The diffraction pattern of 8:2 nanocrystals (FIG. 3 b) show additional peaks at lower diffraction angles, originating from layered structures, along with peaks associated with 3D perovskite formation. Although the (100) and (200) peak intensities are lower for the 8:2 nanocrystals compared to 10:0, the relative intensity difference and peak positions remain unchanged.

In 2D layered perovskites like $(OA)_2PbBr_4$, the inorganic lead halide layers are separated by the second, large organic cations (i.e. large d-spacing). In order to explain the d-spacing values observed in the XRD patterns of the mixed nanocrystals, we recorded the XRD pattern of pure layered $(OA)_2PbBr_4$ (n=1) prepared by a previously reported method (see the examples). This layered compound showed a d-spacing of approximately 10.5 Å. In this case the two dimensional $[PbBr_6]4$ layers are separated by n-octylamine ligands. Knowing the exact d-spacings for the $MAPbBr_3$ and $(OA)_2PbBr_4$, it is possible to conduct a basic elucidation of the varied d-spacings noted in the mixed nanocrystals (without taking strain/solvation effects into consideration). In the XRD patterns of 3:7 and 2:8 nanocrystals (FIGS. 3c and d), the peaks observed at lower diffraction angles correspond well to the expected positions for 2D perovskite layers. For MABr:OABr=3:7, the observed d-spacing values are 10.31, 15.43, 18.7 and 21.4 Å. Similarly, for MABr:OABr=2:8 the observed d-spacing values are 13.69, 15.27, 18.7, and 20.5 Å. The d-spacing of 13.69 Å most likely corresponds to a different layered phase or a different interlayer arrangement of OABr (see the examples).

The varied d-spacings point to the co-crystallization tendency of the organic ammonium perovskites. The high PLQY and stability of the 8:2 nanocrystals could possibly be explained by the formation of such a mixed organic shell. The clear 519 nm PL signature of the nanocrystals indicates that the main emitting species is $MAPbBr_3$. However the weak optical absorption signature at 433 nm points to the possibility of a n=2 shell. Such a higher band-gap shell would allow for efficient confinement and also impart stability. We believe that the observed PLQY and stability enhancement, in combination with the blue-shift in the 8:2 sample originate from the formation of a core-shell type structure, in which the core consists of $MAPbBr_3$ and the shell of layered $(OA)_2PbBr_4$. However, due to the low electron density contrast between the core and the shell, and the structural instability at high magnification, no direct evidence of its formation could be presented using high-resolution (HR)-TEM. Instead, its formation is rationalized via a series of indirect observations from additional experiments (for full details and explanations, see the examples). For example, replacement of the oleylamine ligand with octylamine for MABr:OABr=10:0 resulted in a significantly lower PLQY and a red-shift in PL (see Tables 1 and 4, examples), whereas a similar blue-shift is observed for the 8:2 samples. This implies that OABr is the predominant factor to form a layered perovskite. In order to explore whether the 433 nm signature originates from $(OA)_2MAPb_2Br_7$ (n=2), it was attempted to synthesize spherical $(OA)_2PbBr_4$ nanocrystals using the LARP method without the addition of MABr; the failure to produce the expected nanocrystals suggests that a 3D $MAPbBr_3$ core is essential for the subsequent growth of 2D layers.

Experiments with OA-Br addition after the formation of $MAPbBr_3$ NP seeds (equivalent to MABr:OABr=8:2 and 2:8), resulted in green-emitting nanocrystals with a PL maximum at 522 nm, instead of 519 nm and 438/451 nm, respectively. This further suggests, that only during coprecipitation of MABr and OABr in the presence $PbBr_2$ core-shell type nanoparticles are formed (see the examples). Thermogravimetric analysis provided additional evidence of a structural difference between MABr:OABr 10:0 and 8:2 nanocrystals; both organic components are released at a higher temperature in the 8:2 nanocrystals than the 10:0 nanocrystals, suggesting that additional energy is required to remove intercalated OA-Br from the layered shell (see the examples).

To further understand the PLQY-variation in the mixed organolead bromide nanocrystals, the PL decay kinetics of these nanocrystals were investigated (FIG. 4). The decay curves were fitted with exponential decay functions (the fitted lifetimes and amplitude weighted average lifetimes are provided in the examples). For the perovskite samples with MABr:OABr=10:0 and 8:2, the decays are nearly single-exponential. Their high PLQY, together with the mono-exponential kinetics indicates that the recombination originates predominantly from the radiative exciton decay channels in these nanocrystals. Based on the mono-exponential PL lifetimes ($\tau_{PL}$), the non-radiative recombination lifetimes ($t_{non-rad}$) can be estimated using $\tau_{non-rad}=\tau_{PL}/(1-\phi)$, where $\phi$ is the PLQY. The $\tau_{non-rad}$ in the MABr:OABr=10:0 and 8:2 samples are ~73 and 135 ns, respectively. The longer $\tau_{non-rad}$ in the latter clearly shows a better suppression of the non-radiative channels through improved surface passivation afforded by the growth of the outer shell. On the other hand, for the perovskite nanocrystals with 6:4 to 2:8 MABr:OABr ratios, their transient PL (at their main emission peak) exhibits bi-exponential decay kinetics, with a dominant short (few ns) lifetime component and a longer lifetime (10-20 ns). Nonetheless, the amplitude weighted average exciton lifetime reveals a shortened value ranging from 4.2 to 8.5 ns for these samples (see Table 2 in the examples). The faster decay stems from the presence of non-radiative channels associated with increased defects and surface traps, possibly due to the presence of more 2D perovskite layers, thereby resulting in a lower PLQY for the higher OABr concentrations.

Finally the PL stability of the mixed organolead bromide perovskite nanocrystals was examined (stored under ambient conditions, at 60% RH). The photographs in FIG. 1 d-f show the PL emission under UV exposure at different time intervals. The initially observed 84% PLQY for $MAPbBr_3$ nanocrystals showed a considerable decrease with time and reached a value of 45% after one month and totally quenched after two months (see Table 3, examples). Interestingly, the initially observed 92% PLQY for MABr:OABr=8:2 was found to be more stable and showed only a slight decrease with time and reached a value of 85% after one month and 60% after two months. The 82% PLQY observed for perovskite nanocrystals with 40% OABr reduced to 60% after one month and 20% after two months. Perovskite nanocrystals with a higher amount of OABr showed a fast decay of PL intensity with the increase in time. This may be due to the increase in the lattice strain caused by the increase in the 2D shell thickness. In conclusion, there is provided a new protocol for the synthesis of solution-processed, highly stable and color tunable core-shell type mixed perovskite nanocrystals with a spherical shape and a high PLQY. The cation ratio in the precursor solution is the key factor controlling the layer growth, PLQY and stability of these mixed perovskite nanocrystals (NCs).

By the aid of the quantum confinement effect, these core-shell type mixed perovskite nanocrystals possess large multiphoton absorption and high PLQY and are suitable for nonlinear optical applications, such as optical limiting, multiphoton excited PL/lasing. Furthermore, a high band-gap 2D shell, for example an octylammonium lead bromide $(OA)_2PbBr_4$ shell (~3 eV), was developed using a similar protocol to coat the lower band gap NC core. As a comparative example, all-inorganic perovskite ($CsPbBr_3$) NCs (cuboidal shape) have been reported to possess exceptional two-photon absorption property at 800 nm with two-photon action cross-section around 2 orders larger than the conventional semiconductor NCs and organic molecules, serving as a new benchmark for two-photon absorbing materials. In order to demonstrate the outstanding multiphoton absorption properties achieved in the 3D core and multidimensional core-shell type organic-inorganic perovskite NCs as presently disclosed, their multiphoton action cross-sections to that of $CsPbBr_3$ NCs was compared. Even larger (about 3 times) multiphoton action cross-sections than that of $CsPbBr_3$ NCs were achieved in the multidimensional core-shell type organic-inorganic perovskite NCs as presently disclosed. The insets of FIG. 14 a-c exemplary show the TEM images of the $MAPbBr_3$ NCs, $MAPbBr_3/(OA)_2PbBr_4$ core-shell type NCs (with MABr and OABr molar ratio 8:2), and $CsPbBr_3$ NCs.

Here, there is reported a breakthrough in achieving giant five-photon absorption and highly efficient upconversion fluorescence using multidimensional core-shell perovskite colloidal NCs. Organic chromophores and conventional semiconductor NCs are considered leaders in two-/three-photon absorption applications, but they face considerable challenges from their small five-photon (5P) action cross-sections ($\eta\sigma_5$). To date, there has only been one report of 5P excited upconversion fluorescence in the literature using carefully designed and synthesized organic chromophore; while 5P excited upconversion fluorescence from semiconductor NCs has yet to be demonstrated. Herein, the 3D core and multidimensional core-shell organic-inorganic perovskite NCs (e.g., $MAPbBr_3$, and $MAPbBr_3/(OA)_2PbBr_4$ NCs) transcend these challenges with highly efficient five-photon excited upconversion fluorescence—an unprecedented feat for semiconductor NCs. Multidimensional type-I core-shell perovskite nanocrystals (for example, three-dimensional $MAPbBr_3$ core encapsulated with two-dimensional $(OA)_2PbBr_4$ perovskite shell) exhibits $\eta\sigma_5$ at least 9-orders larger than state-of-the-art specially-designed organic molecules. These findings will therefore open fresh approaches for next generation multiphoton imaging applications with unmatched imaging depth, sensitivity and resolution.

Several aspects of this disclosure include:
First realization of five-photon absorption and resultant highly efficient upconversion fluorescence in halide perovskite colloidal NCs excited at IR wavelengths (~2 µm). This effectively overcomes the inherent challenges of small five-photon action cross-sections in organic chromophores and conventional semiconductor NCs.
First investigation, and detailed characterization of the multiphoton (2-, 3-, 4-, 5-photon) action cross-sections of the halide perovskite colloidal NCs over the wide excitation wavelength range of 675-2300 nm.
First report on further achieving large enhancement of multiphoton action cross-sections in perovskite colloidal NCs utilizing a multidimensional core-shell structure.
An unprecedented 9-orders larger five-photon action cross-sections ($\eta\sigma_5 \sim 10^{-136}$ $cm^{10}s^4$ $photon^{-4}$) than state-of-the-art specially-designed organic molecules is observed in multidimensional core-shell perovskite NCs, demonstrating the potential for next generation multiphoton imaging applications with unmatched imaging depth, sensitivity and resolution.

These new insights challenge the conventional knowledge of multiphoton absorption in colloidal semiconductor NCs and enable fresh approaches for next generation of optical power limiting, low-threshold upconversion lasing and especially, multiphoton imaging applications. Below, a detailed description of the experimental and theoretical investigations is presented, which includes linear optical properties and structural characterization (incl. density function theory modelling); Five-photon absorption from the 3D core (for example $MAPbBr_3$) and multidimensional core-shell type ($MAPbBr_3/(OA)_2PbBr_4$) organic-inorganic perovskite NCs, and their comparison to that of 3D all-inorganic $CsPbBr_3$ NCs; Multiphoton excited frequency-upconverted photoluminescence (PL) measurements and characterization of multiphoton action cross-section spectra in the halide perovskite NCs; Open-aperture Z-scan measurements for quantification of the 2 PA cross-sections at 800 nm and 3 PA cross-sections at 1050 and 1100 nm; time-resolved PL measurements and discussion on the underlying physical mechanisms for the largely enhanced multiphoton action cross-sections of the multi-dimensional core-shell perovskite NCs.

EXAMPLES

Experimental Section

Example 1

Materials:
Lead bromide, $PbBr_2$ (99.999%, trace metals basis, Sigma-Aldrich); oleic acid, OAc (90%, Sigma-Aldrich); oleylamine, OAm (70%, Sigma-Aldrich); N,N-Dimethylformamide, DMF (Anhydrous, 99.8%, Sigma-Aldrich); octylamine (99%, Sigma-Aldrich); butylamine (99.5%, Sigma-Aldrich); dodecylamine (99%, Sigma-Aldrich); toluene (Anhydrous, 99.7% GC, Sigma-Aldrich); hydrobromic acid, HBr (48%, Sigma-Aldrich); methylammonium bromide, MABr (Dyesol). All these chemicals were used without further purification.

Example 2

Synthesis of Different Cationic Ammonium Bromide Powder:
OABr was synthesized by mixing octylamine and HBr.
At first octylamine was precooled in a glass beaker to 0° C. under vigorous stirring condition and HBr was added dropwise. The reacted solution was stirred for 2 hours. The reaction mixture was then transferred to a rotary evaporator to remove the solvent. The resulting precipitate was washed several times with diethylether to remove impurities and then dried in a vacuum furnace overnight at 60° C. to get a purified white colored $CH_3(CH_2)_7NH_3Br$ powder. The butylammonium bromide (BABr) and dodecylammonium bromide (DDABr) powders were synthesized by same synthetic procedure while changing the methylamine to butylamine and dodecylamine respectively.

Example 3

Synthesis of $MAPbBr_3$ and Mixed Cation Organo Lead Bromide NPs:

$MAPbBr_3$ NPs were synthesized by LARP method as reported elsewhere. At first in a glass vial 0.16 mmol of MABr, 0.2 mmol of $PbBr_2$ were mixed in 5 mL DMF solution. Later 50 μL of OAm and 0.5 mL OAc were also mixed in the DMF solution to form the final precursor solution.

Another round bottom glass flask containing 5 mL of toluene was heated at 60° C. in an oil bath. Then 250 μL of as prepared precursor solution was swiftly injected into toluene under vigorous stirring condition. The solution turned into green color confirms the formation of $MAPbBr_3$NPs. The reaction was continued for 5 min and transferred into a centrifuge tube. The NPs were purified by centrifugation method that centrifuged at 7000 rpm for 10 min. The precipitate was discarded and the supernatant was collected for further characterization.

For mixed cation organo MA-OA, BA-OA and DDA-OA lead bromide NPs were synthesized by the same synthetic procedure elaborated above. Here we maintained the same total molar concentration of alkyl ammonium bromide inside the precursor solution. The molar ratio of MABr and OABr were varied to 8:2, 6:4, 4:6, 3:7, and 2:8. The molar ratio of BABr-OABr and DDABr-OABr was fixed to 8:2.

Example 4

Seeded (Modified) Synthesis Attempt of Mixed Cation Organo Lead Bromide NPs:

In the modified synthesis, the same LARP synthetic protocol was followed as described above. Here at first there was injected $MABr-PbBr_2$ precursor solution into toluene to grow $MAPbBr_3$ NPs first and later the desired amount of $OABr-PbBr_2$ precursor solution was injected.

Example 5

Synthesis of $(OA)_2PbBr_4$ Nanodisks:

$(OA)_2PbBr_4$ nanodisks were synthesized by one-pot synthetic approach as reported elsewhere. At first in a glass vial 0.4 mmol of octylamine, 0.1 mmol of $PbBr_2$ were mixed in 200 μL DMF solution. Later 50 μL of HBr was mixed in this DMF solution to form the final precursor solution. In another glass beaker this precursor solution was added dropwise in 2 mL of hexane under vigorous stirring condition at room temperature. After 5 min the reaction was stopped by adding 3 mL of acetone and then centrifuged at 4500 rpm for 10 min. The precipitate obtained was collected for structural and photophysical studies.

Example 6

Structural and Photophysical Studies:

The absorbance spectra of the perovskite NPs in solution phase were recorded by Shimadzu UV1800 UV-VIS Spectrophotometer and PL spectra was recorded by Shimadzu RF-5301pc Spectrofluorophotometer. The absolute PLQY was measured by Ocean-optics USB4000 spectrometer with an integrated sphere excited at 400 nm laser beam. X-Ray diffraction analysis was carried out with XRD Bruker D8 Advance. The time-resolved PL was recorded by an Optronis Optoscope streak camera system. The excitation source is 400 nm femtosecond laser with pump intensity of 0.2 $\mu J/cm^{-2}$. The imaging of the NPs was recorded by transmission electron microscopy (TEM, Jeol JEM-2010). The morphological imaging was carried out using field emission scanning electron microscopy (FESEM, JEOL JSM-7600F).

TABLE 1

Details of the photophysical properties observed for mixed organo lead bromide perovskite NPs with different molar ratio of cations with oleylamine as the capping ligand.

| MABr:OABr | Absorbance peak position (nm) | PL peak position (nm) | PL FWHM (nm) | PLQY (%) |
|---|---|---|---|---|
| 10:0 | 513 | 521 | 24 | 84 |
| 8:2 | 433, 510 | 519 | 26 | 92 |
| 6:4 | 397, 422, 502 | 512 | 37 | 82 |
| 4:6 | 397, 433, 450, 471, 486 | 456, 476, 490 | 55 | 55 |
| 3:7 | 397, 433, 451 | 438, 456, 474 | 25 | 30 |
| 2:8 | 397, 433 | 438, 451 | 23 | 21 |

TABLE 2

Fitted PL lifetimes and the corresponding amplitude values. The 10:0 and 8:2 samples are fitted with single exponential decay and the others are fitted with bi-exponential decay functions. $\tau_{avg} = A_1\tau_1 + A_2\tau_2$.

| MABr:OABr | $A_1$ | $\tau_1$ (ns) | $A_2$ | $\tau_2$ (ns) | $\tau_{avg}$ (ns) |
|---|---|---|---|---|---|
| 10:0 | 1 | 11.7 ± 0.1 | — | — | — |
| 8:2 | 1 | 10.8 ± 0.1 | — | — | — |
| 6:4 | 0.59 | 6.2 ± 0.1 | 0.41 | 2.0 ± 0.1 | 2.0 ± 0.1 |
| 3:7 | 0.79 | 2.2 ± 0.1 | 0.21 | 2.0 ± 0.1 | 2.0 ± 0.1 |
| 2:8 | 0.84 | 2.0 ± 0.1 | 0.16 | 2.0 ± 0.1 | 2.0 ± 0.1 |

TABLE 3

PLQY obtained for the mixed organo lead bromide perovskite NPs in different time intervals.

| MABr:OABr | PLQY (%) (during synthesis) | PLQY (%) (after one month) | PLQY (%) (after two months) |
|---|---|---|---|
| 10:0 | 84 | 45 | 0 |
| 8:2 | 92 | 85 | 60 |
| 6:4 | 82 | 60 | 20 |
| 4:6 | 55 | 30 | 0 |
| 3:7 | 30 | 10 | 0 |
| 2:8 | 21 | 0 | 0 |

TABLE 4

Photospectroscopic data observed for mixed organo lead bromide perovskite NPs with different molar ratio of cations with octylamine as the capping ligand.

| MABr:OABr | Absorbance peak position (nm) | PL peak position (nm) | PL FWHM (nm) | PLQY (%) |
|---|---|---|---|---|
| 10:0 | 509 | 523 | 20 | 67 |
| 8:2 | 433, 507 | 521 | 22 | 58 |
| 6:4 | 433, 450, 470, 486 | 501 | 36 | 52 |

TABLE 4-continued

Photospectroscopic data observed for mixed organo
lead bromide perovskite NPs with different molar ratio
of cations with octylamine as the capping ligand.

| MABr:OABr | Absorbance peak position (nm) | PL peak position (nm) | PL FWHM (nm) | PLQY (%) |
|---|---|---|---|---|
| 4:6 | 433, 450, 471, 486 | 457, 477, 493 | 38 | 47 |
| 3:7 | 433, 451 | 438, 455, 472 | 40 | 38 |
| 2:8 | 397, 433 | 438, 451 | 28 | 25 |

Example 7—Linear Optical Properties and Structural Characterization (Incl. Density Function Theory Modelling)

Briefly, the core-only MAPbBr$_3$ NCs and core-shell MAPbBr$_3$/(OA)$_2$PbBr$_4$ NCs are of spherical shape with diameters of ca. 8-9 nm and 9-10 nm, respectively. Whereas, the comparison standard (i.e., CsPbBr$_3$ NCs) are approximately 9 nm-sized of cuboidal shape. The one-photon absorption (1 PA) and one-photon-excited PL spectra of the MAPbBr$_3$, MAPbBr$_3$/(OA)$_2$PbBr$_4$ and CsPbBr$_3$ NCs in toluene are displayed in FIG. 14 a-c. The 1 PA peaks of MAPbBr$_3$ and MAPbBr$_3$/(OA)$_2$PbBr$_4$ NCs are located at approximately 510 nm and 511 nm, while their corresponding excitonic PL peaks are located at ~521 nm (full-width at half maximum (FWHM) ~22.5 nm) and ~520 nm (FWHM ~24.5 nm), respectively. On the other hand, the colloidal CsPbBr$_3$ NCs solution in toluene exhibited an absorption peak at ~505 nm and an excitonic PL peak at ca. 513.5 nm with narrow FWHM ~21 nm. The clear blue shifts of approximately 15 and 45 nm compared to their bulk counterparts, respectively, is evidence of quantum confinement in the organic-inorganic and all-inorganic hybrid perovskite NCs. The smaller blue shift in MAPbBr$_3$ NCs stems from its smaller Bohr diameter ($d_B$~4 nm) compared to CsPbBr$_3$ NC ($d_B$~7 nm). The relatively weaker quantum confinement in MAPbBr$_3$ NCs (i.e., weak confinement $d_B$<<8-9 nm) thus gives rise to their smaller MPA cross-sections than CsPbBr$_3$ NCs ($d_B$ comparable to 9 nm) as discussed in following section. On the other hand, even larger MPA than CsPbBr$_3$ NCs was achieved through coating the MAPbBr$_3$ NCs with a 2D layered (OA)$_2$PbBr$_4$ shell as shown in following section. The PLQY of MAPbBr$_3$ NCs was measured to be ~84%, lower than the core-shell MAPbBr$_3$/(OA)$_2$PbBr$_4$ NCs (~84 vs ~92%), where the latter also exhibited much better colloidal stability under ambient conditions, retaining ca. 60% PLQY after two months storage. Both the enhanced PLQY and the improved stability is achieved by coating the MAPbBr$_3$ core with the layered perovskite shell; thus not only providing dielectric confinement, but also effective surface passivation. In comparison, the PLQY of CsPbBr$_3$ NCs was approximately 55%, close to the reported literature values.

Figure 14:
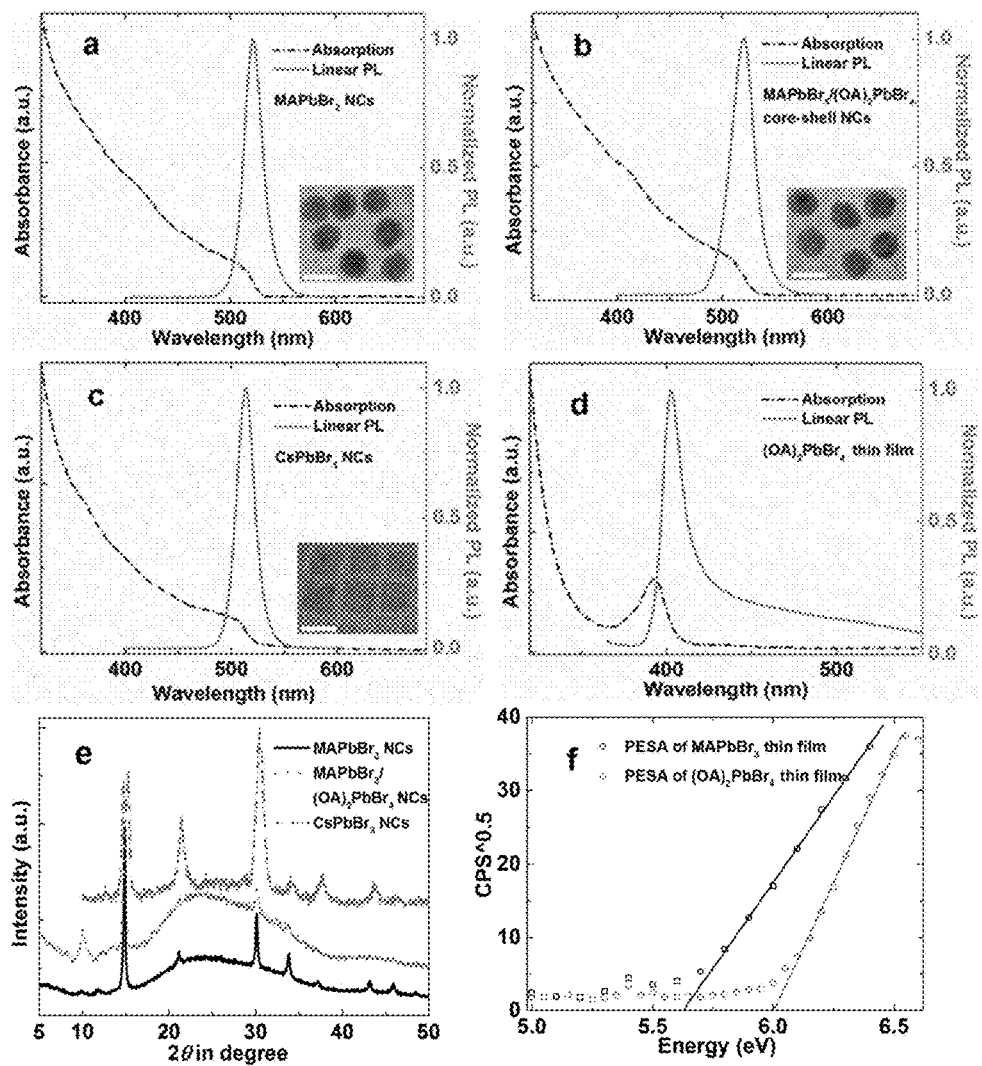
FIG. 14 shows 1 PA spectra and one-photon excited PL spectra, TEM images, XRD patterns of the perovskite NCs and PESA measurements: (a-c) 1 PA spectra and one-photon excited PL spectra of the MAPbBr$_3$, MAPbBr$_3$/(OA)$_2$PbBr$_4$ and CsPbBr$_3$ NCs, respectively, together with their representative TEM images (scale bar, 10 nm) shown in the inset; (d) 1 PA spectra and one-photon excited PL spectra of the (OA)$_2$PbBr$_4$ thin film; (e) XRD patterns of the MAPbBr$_3$, MAPbBr$_3$/(OA)$_2$PbBr$_4$ and CsPbBr$_3$ NCs; (f) PESA results from the MAPbBr$_3$ and (OA)$_2$PbBr$_4$ thin films.
Figure 15:
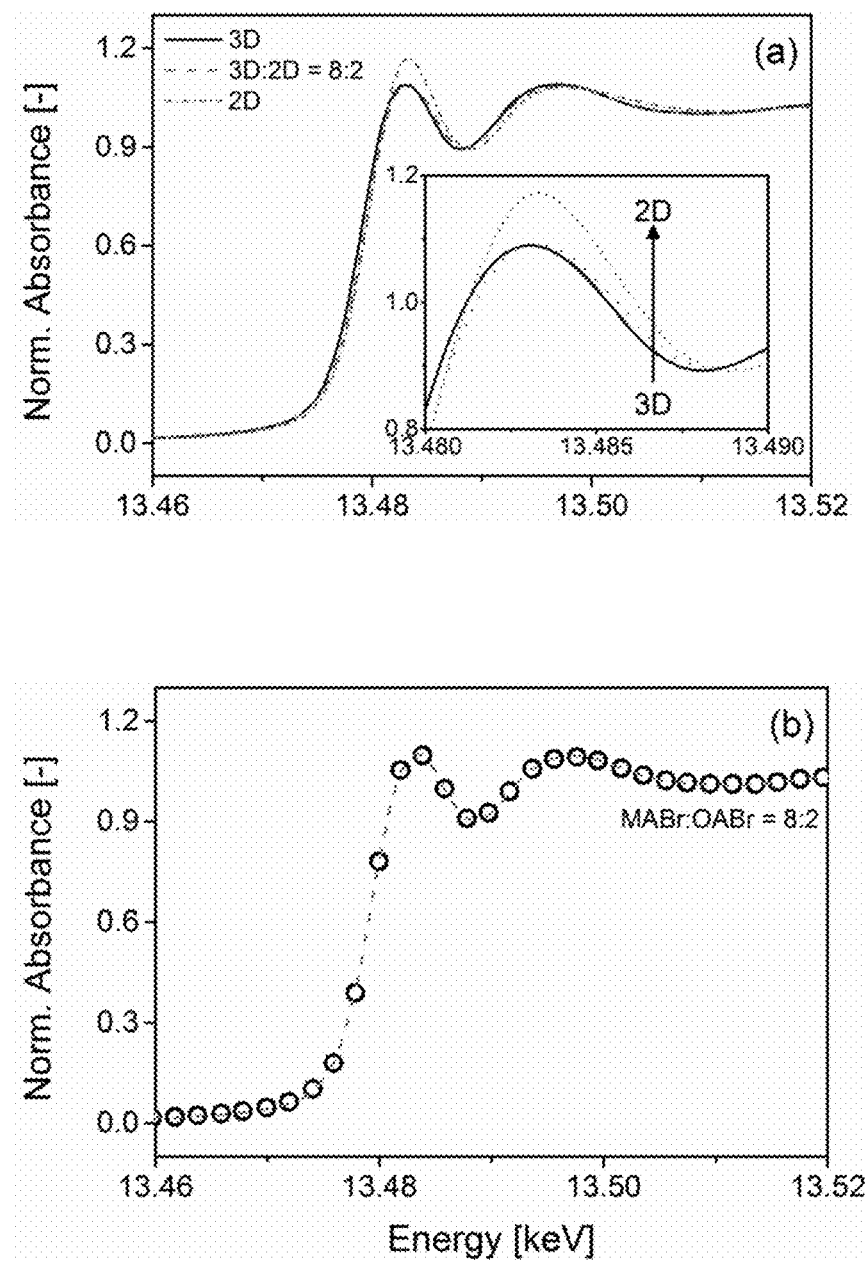
FIG. 15 shows X-ray absorption spectroscopy (XAS) measurements performed at the Beijing Synchrotron Radiation Facility (BSRF), where 'pure' MAPbBr$_3$ (3D) and (OA)$_2$PbBr$_4$ (2D) NCs were used as reference materials. (a) Overview of XAS spectra for core-shell NCs prepared with MABr:OABr ratios of 8:2 compared to the reference materials. Inset: magnification around the absorption edge. (b) Linear fit models for NCs synthesized with MABr:OABr=8:2. The fit is based on the linear absorption contribution of both reference samples.

The XRD patterns of the MAPbBr$_3$ core, MAPbBr$_3$-(OA)$_2$PbBr$_4$ core-shell type and CsPbBr$_3$ NCs are displayed in FIG. 14 e. The XRD peak positions for the MAPbBr$_3$ NCs and CsPbBr$_3$ NCs (FIG. 14 e) match well with the cubic structure of reported patterns for the bulk system, with a d-spacing of around 5.9 Å. The diffraction pattern of MAPbBr$_3$/(OA)$_2$PbBr$_4$ NCs shows additional peaks at lower diffraction angles, originating for layered (OA)$_2$PbBr$_4$) structures, along with peaks associated with 3D perovskite formation. The presence of the 2D layered shell was further corroborated by employing X-ray absorption spectroscopy (XAS) using synchrotron radiation. By probing the Br-edge absorption, differences in the local electronic and geometric structures of 3D and 2D perovskites are expected. The normalized absorption spectra of MABr:OABr 8:2 and 4:6 samples were used to directly reveal structural changes as compared to the pure MAPbBr$_3$ (3D) and (OA)$_2$PbBr$_4$ (2D) materials, as shown in FIG. 15. The samples were fit using a linear contribution of both 3D and 2D components, revealing that both phases contribute to the absorption, and a (OA)$_2$PbBr$_4$ deficiency occurs at higher OABr concentration (i.e. 8:2 and 4:6 are actually 92:8 and 71:29, respectively).

Figure 17:
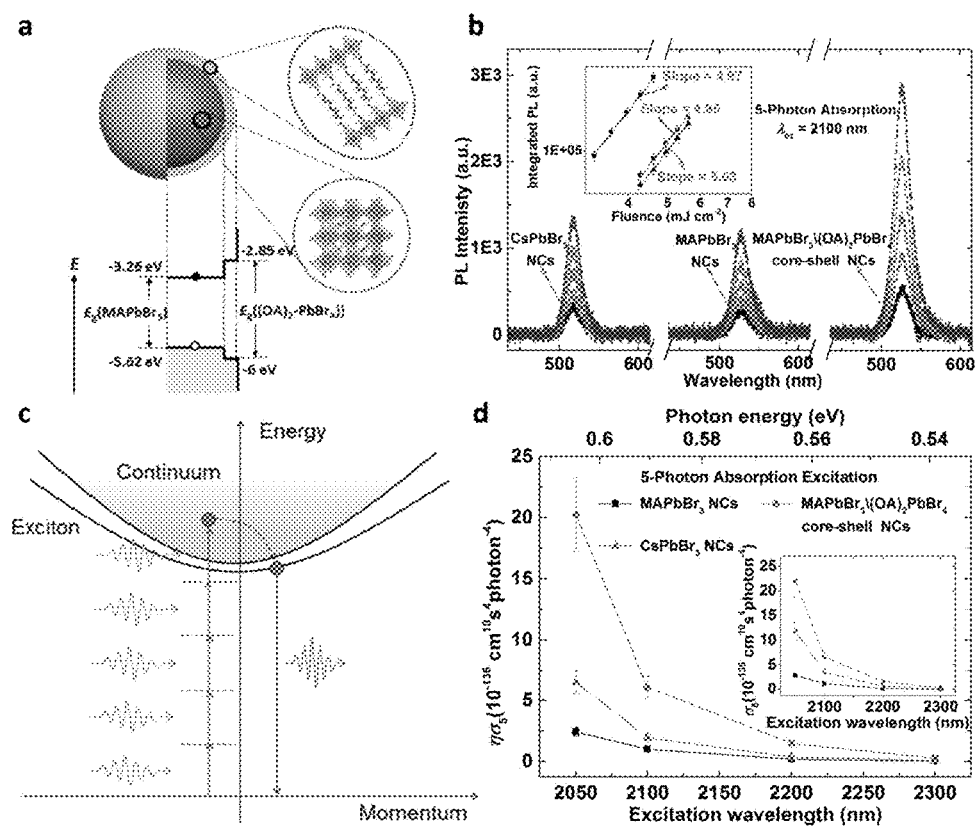
FIG. 17 shows type I core-shell multi-dimensional perovskite NCs and their ultra-large five-photon action cross-sections ($\eta\sigma_5$). (a) Schematic illustrating the core-shell multi-dimensional perovskite NCs with 3D MAPbBr$_3$ as core and 2D (OA)$_2$PbBr$_4$ as shell, and their type-I energy level alignment; (b) 5PPL spectra from core-only MAPbBr$_3$ NCs (~2.0 µM in toluene), core-shell MAPbBr$_3$/(OA)$_2$PbBr$_4$ NCs (~2.1 µM in toluene) and CsPbBr$_3$ NCs (~1.0 µM in toluene), with femtosecond laser excitation at 2100 nm. Inset shows the quintic dependence on the excitation fluence of the spectrally integrated PL intensity; (c) Schematic illustrating the 5PPL process in perovskite NCs; (d) five-photon action cross-section ($\eta\sigma_5$) spectra of the MAPbBr$_3$, MAPbBr$_3$/(OA)$_2$PbBr$_4$ and CsPbBr$_3$ NCs. Error bars indicate experimental uncertainty of ±15%.

Photo electron spectroscopy in air (PESA) measurements on MAPbBr$_3$ and (OA)$_2$PbBr$_4$ thin films were performed to estimate the valance band maximum (VBM) alignment between the core and shell in the core-shell MAPbBr$_3$/(OA)$_2$PbBr$_4$ NCs (FIG. 14 f), and to avoid the influence from the organic ligands on surface of NCs films. The PESA results reveal a VBM at −5.62 and −6.00 eV for MAPbBr$_3$ and (OA)$_2$PbBr$_4$ thin films, respectively. These results, combined with the optical bandgap measurements (FIG. 14 a-c), imply that a type-I conduction and valence band-edge alignment between the core and shell in the MAPbBr$_3$/(OA)$_2$PbBr$_4$ NCs is expected (as shown in FIG. 17 a).

In order to theoretically investigate the conduction and valence band-edge alignment between the core and shell in the core-shell NCs, there was employed the all-electron-like projector augmented wave (PAW) method and the Perdew-Burke-Ernserhof (PBE) exchange correlation potential, as implemented in the VASP code. The resulting band offset of MAPbBr$_3$/(OA)$_2$PbBr$_4$ is then given by:

$$\Delta E_{VBM} = (E_{VBM}^{bulk}(MAPbBr_3) - E_{1s}^{bulk}(MAPbBr_3)) - \qquad (1)$$
$$(E_{VBM}^{bulk}((OA)_2PbBr_4) - E_{1s}^{bulk}((OA)_2PbBr_4)) +$$
$$(E_{VBM}^{if}(MAPbBr_3) - E_{VBM}^{if}((OA)_2PbBr_4))$$

Figure 16:
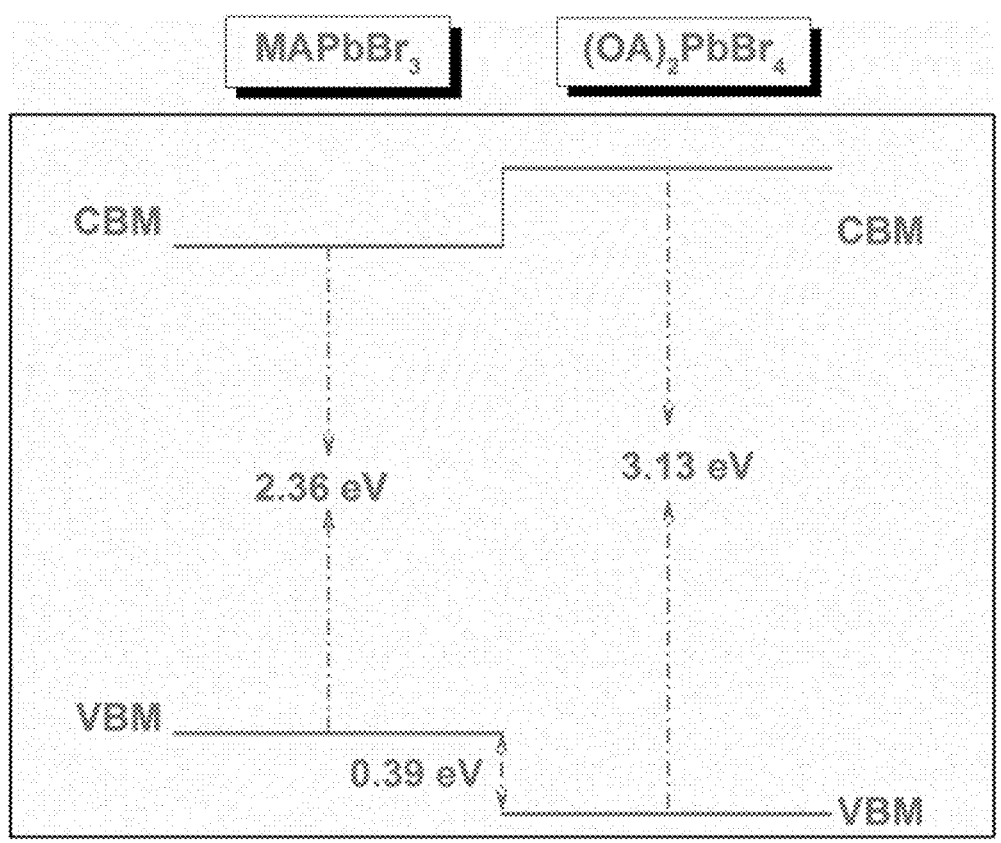
FIG. 16 show the band offset of MAPbBr$_3$/(OA)$_2$PbBr$_4$: The VBM difference (0.39 eV) is from theoretical calculations and the band gaps are experimental values.

The calculated band offset of MAPbBr$_3$/(OA)$_2$PbBr$_4$ NCs is presented in FIG. 16, where the band gaps are experimental values. We find that the VBM of MAPbBr$_3$ is 0.39 eV higher than (OA)$_2$PbBr$_4$, which is in good agreement with the experimental result (0.38 eV). A type-I band offset was revealed by the theoretical results.

Example 8—Giant Five-Photon Absorption from Perovskite Colloidal NCs

The schematic illustration of the type-I conduction and valence band edge alignment between the core and shell in the core-shell MAPbBr$_3$/(OA)$_2$PbBr$_4$ NCs is displayed in FIG. 17 a, as validated by the aforementioned PESA measurements and theoretical calculations. FIG. 17 b shows the 5P-excited (i.e., at 2100 nm wavelength) excitonic PL emission (centred around 520 nm) from the MAPbBr$_3$ core, MAPbBr$_3$-(OA)$_2$PbBr$_4$ core-shell type NCs compared with that of CsPbBr$_3$ NCs, and their quintic excitation fluence dependence (inset). The 5 PA excitation process via virtual energy levels is schematically illustrated in FIG. 17 c. FIG. 17 d shows the ultra-large $\eta\sigma_5$ (and their corresponding $\sigma_5$ values (inset)) obtained through employing the $\sigma_2$ values at 800 nm measured by Z-scan (FIG. 18, 19 b-d) as a standard and applying the multiphoton-excited frequency-upconverted PL calculation equations (i.e., Eqs. (2)-(6) as shown later) for these halide perovskite colloidal NC samples over the IR excitation wavelengths of 2050-2300 nm. Record $\eta\sigma_5$~$10^{-136}$ cm$^{10}$s$^4$ photon$^4$ values are achieved with MAPbBr$_3$/(OA)$_2$PbBr$_4$ NCs>CsPbBr$_3$ NCs>MAPbBr$_3$ NCs (see Table 5); highlighting the significance of the (OA)$_2$PbBr$_4$ shell to enhance the nonlinear optical absorption action cross-sections. All three samples follow a similar spectral dependence with $\eta\sigma_5$ for MAPbBr$_3$/(OA)$_2$PbBr$_4$ NCs about 6-8 times larger than MAPbBr$_3$ NCs and about 3 times larger than CsPbBr$_3$ NCs (see Table 5).

TABLE 5

Multi-photon action cross-sections $\eta\sigma_n$ of hybrid halide perovskite NCs over their respective wavelength range[#]

| | Multi-photon excitation | |
|---|---|---|
| Perovskite NCs | Two-photon $\eta\sigma_2$ (10$^6$ GM) (675-1000 nm) | Three-photon $\eta\sigma_3$ (10$^{-74}$ cm$^6$s$^2$photon$^{-2}$) (1050-1500 nm) |
| MAPbBr$_3$ | 0.41 ± 0.06 to 5.2 ± 0.8 | 0.33 ± 0.05 to 2.7 ± 0.4 |
| MAPbBr$_3$/ (OA)$_2$PbBr$_4$ | 3.0 ± 0.4 to 37 ± 6 | 2.5 ± 0.4 to 22 ± 3 |
| CsPbBr$_3$ | 0.97 ± 0.15 to 13 ± 2 | 0.38 ± 0.06 to 7.6 ± 1.1 |

| | Multi-photon excitation | |
|---|---|---|
| Perovskite NCs | Four-photon $\eta\sigma_4$ (10$^{-104}$ cm$^8$s$^3$photon$^{-3}$) (1550-2000 nm) | Five-photon $\eta\sigma_5$ (10$^{-136}$ cm$^{10}$s$^4$photon$^{-4}$) (2050-2300 nm) |
| MAPbBr$_3$ | 0.036 ± 0.005 to 3.0 ± 0.5 | 0.039 ± 0.006 to 2.4 ± 0.4 |
| MAPbBr$_3$/ (OA)$_2$PbBr$_4$ | 0.21 ± 0.03 to 24 ± 4 | 0.29 ± 0.04 to 20 ± 3 |
| CsPbBr$_3$ | 0.071 ± 0.011 to 6.9 ± 1.0 | 0.092 ± 0.014 to 6.5 ± 1.0 |

[#]The experimental error ±15% stems mainly from the uncertainty in fluctuation of input laser pulse energy and determination of laser beam characteristics such as pulse duration and minimum beam waist, which are essential for both open-aperture Z-scan and MEPL measurements.

Figure 20:
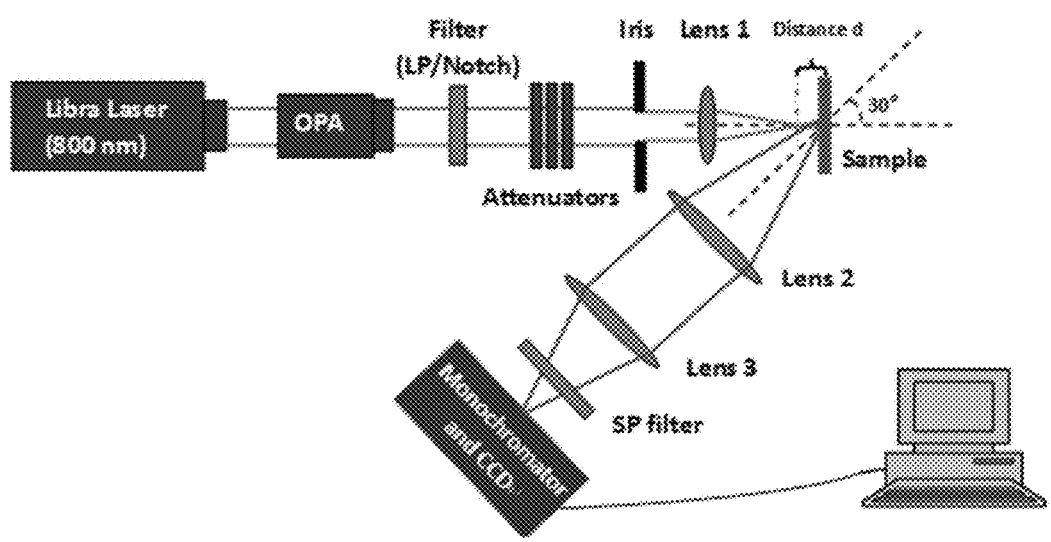
FIG. 20 show the experimental setup for MEPL measurements: The excitation wavelengths were varied from 675 nm to 2300 nm to investigate two-, three-, four- and five-photon absorption excited PL. OPA, LP and SP are abbreviations for optical parametric amplifier, long-pass filter and short-pass filter. For $\lambda_{ex}$<800 nm, a notch filter at 800 nm was utilized to block off the light at undesired wavelengths. For $\lambda_{ex}$>800 nm, an appropriate long-pass filter (at 750 nm or at 1500 nm) was applied to filter out light at unwanted wavelengths. A circular lens (f=20 cm) was applied to focus laser pulses onto the perovskite NCs in toluene solution. The NC samples were placed 3.5 cm away from the focal point to avoid high excitation peak intensity and to have larger excitation area (thus larger signal). Frequency-upconverted PL was collected at a backscattering angle of 150° into an optical fibre which was coupled into a spectrometer and detected by a charge coupled device. A short-pass filter (650 nm) was employed to filter out the scattered light at the excitation laser frequencies.
Figure 21:
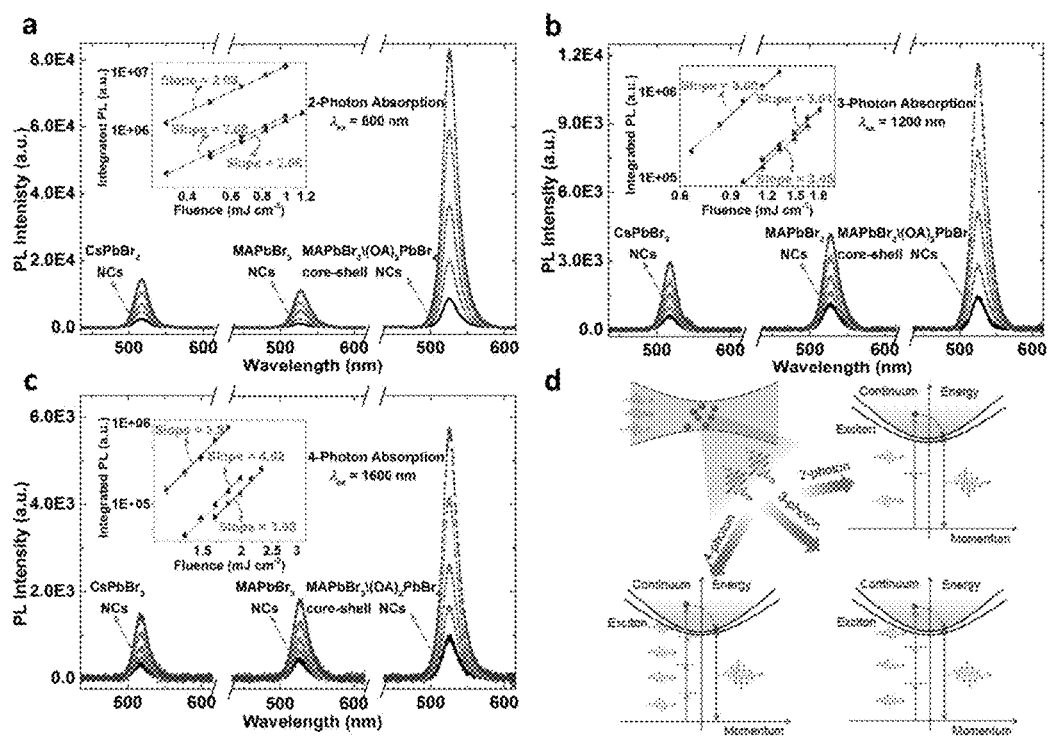
FIG. 21 shows two, three, and four-photon excited upconversion PL spectra from toluene solution of perovskite NCs, insets indicate their excitation fluence dependence by the log-log plots of spectrally integrated PL intensity vs excitation laser fluences. (a-c) Two-, three- and four-photon-absorption excited PL spectra from toluene solutions of MAPbBr$_3$ NCs (~2.0 µM), MAPbBr$_3$/(OA)$_2$PbBr$_4$ NCs (~2.1 µM) and CsPbBr$_3$ NCs (~1.0 µM) excited by fs laser beam at 800, 1200, 1600 nm, respectively. Insets are their corresponding quadratic, cubic and quartic dependence on the excitation fluence; (d) Schematic illustrating the processes of 2 PPL, 3 PPL and 4PPL in the perovskite NCs corresponding to (a-c).
Figure 22:
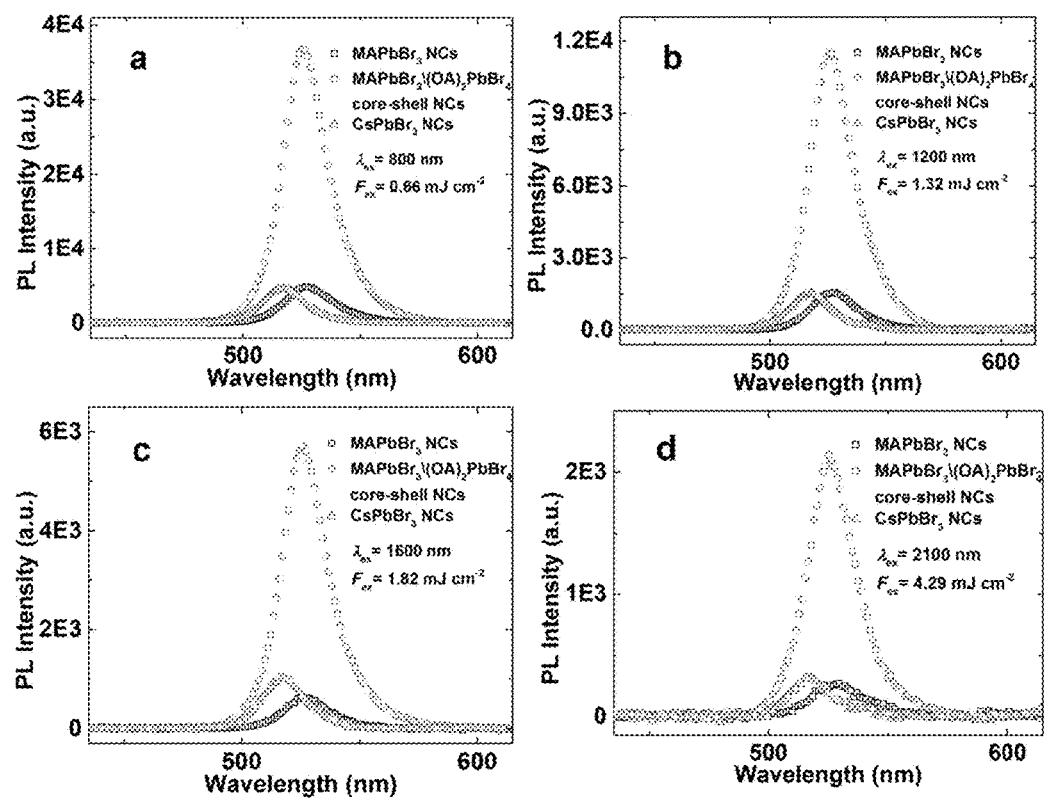
FIG. 22 shows a comparison of the MEPL (2, 3, 4, and 5-photon) from the toluene solution of perovskite NCs excited at 800, 1200, 1600, and 2100 nm (a) Comparison of the two-photon-excited frequency-upconverted PL at 800 nm from the core-only MAPbBr$_3$ NCs (~2.0 µM), core-shell MAPbBr$_3$/(OA)$_2$PbBr$_4$ NCs (~2.1 µM) and CsPbBr$_3$ NCs (~1.0 µM) under the same excitation fluence of ~0.66 mJ cm$^{-2}$; (b) Comparison of the three-photon-excited frequency-upconverted PL at 1200 nm from the perovskite NCs under the excitation fluence of 1.32 mJ cm$^{-2}$; (c) Comparison of the four-photon-excited frequency-upconverted PL at 1600 nm from the perovskite NCs under the excitation fluence of ~1.82 mJ cm$^{-2}$; (d) Comparison of the five-photon-excited frequency-upconverted PL at 2100 nm from the perovskite NCs under the excitation fluence of ~4.29 mJ cm$^{-2}$.
Figure 24:
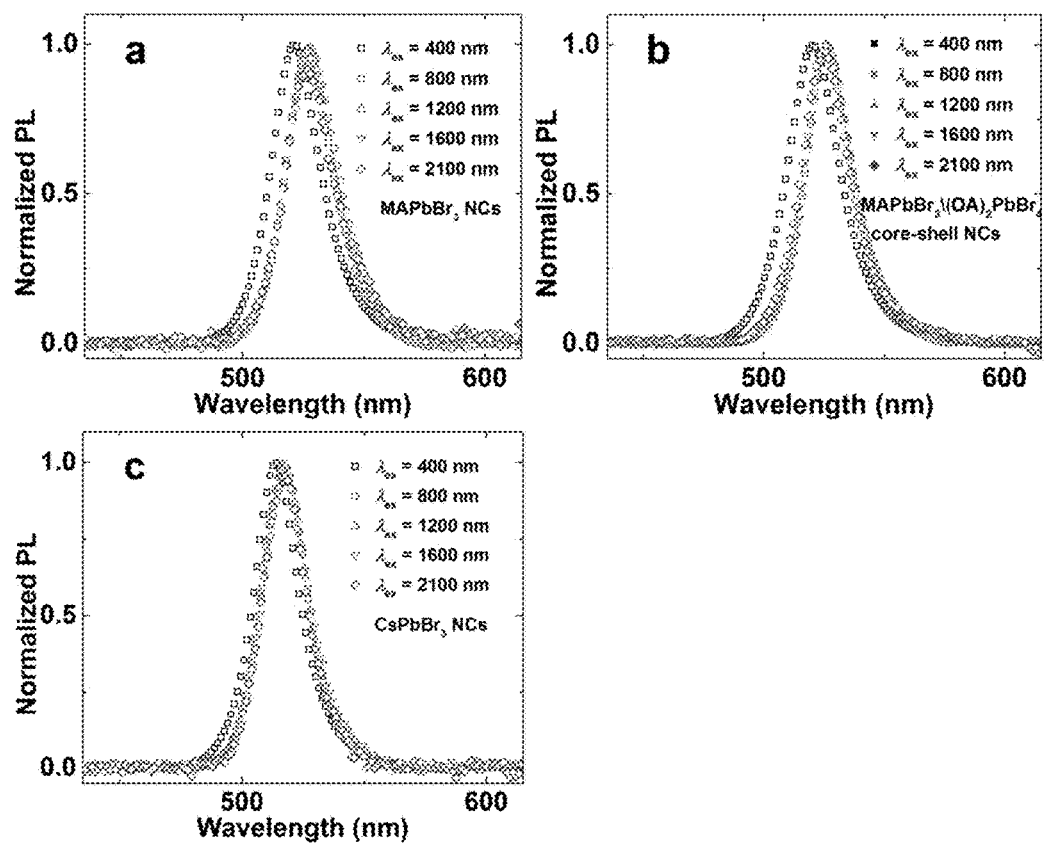
FIG. 24 shows a comparison of the normalized one-photon-excited and multi-photon-excited PL spectra from perovskite NCs (a-c) Comparison of the normalized one-photon-excited and multi-photon-excited PL spectra from MAPbBr$_3$, MAPbBr$_3$/(OA)$_2$PbBr$_4$ and CsPbBr$_3$ NCs, respectively.

Example 9—Multiphoton Excited Frequency-Upconverted Photoluminescence (PL) Measurements and Characterization of Multiphoton Action Cross-Section Spectra in Perovskite NCs Multi-photon excited photoluminescence (MEPL) from MAPbBr$_3$, MAPbBr$_3$/(OA)$_2$PbBr$_4$ dispersed in toluene were investigated at room temperature by utilizing fs laser pulses with excitation wavelengths ranging from 675 to 2300 nm for excitation. For comparison purpose, MEPL from toluene solution of CsPbBr$_3$ NCs were also studies under the same excitation condition. Dilute colloidal NC solutions in toluene, contained in 2-mm-thick quartz cuvettes, were employed for the MEPL measurements. FIG. 20 displays a schematic diagram of the experimental set-up. Similar to FIG. 17 b, MEPL spectra under 2, 3 and 4-photon excitation for the NCs at 800, 1200, 1600 nm are shown in FIG. 21 a-c; and illustrated schematically in FIG. 21 d. FIG. 21 a-c insets clearly shows the nearly quadratic, cubic and quartic dependences of the spectrally integrated PL intensity on excitation fluence for the 2-, 3- and 4-photon processes, respectively. Comparison between the MEPL from MAPbBr$_3$ and MAPbBr$_3$/(OA)$_2$PbBr$_4$ NCs to that from CsPbBr$_3$ NCs under the same excitation fluence at 800, 1200, 1600 and 2100 nm are displayed in FIG. 22. FIG. 22 clearly indicates the much larger MEPL in the core-shell MAPbBr$_3$/(OA)$_2$PbBr$_4$ NCs than the core-only MAPbBr$_3$ NCs, consistent with photos shown in FIG. 23. CsPbBr$_3$ NCs with smaller concentration display MEPL with similar amplitude to MAPbBr$_3$ NCs as presented in FIG. 22, in accordance with photos in FIG. 23 and demonstrating their larger multiphoton action cross-sections. On the other hand, much larger MEPL was achieved in the core-shell MAPbBr$_3$/(OA)$_2$PbBr$_4$ NCs than the CsPbBr$_3$ NCs, indicating their greater multiphoton action cross-sections. Further excitation fluence dependent MEPL measurements at wavelengths ranging from 675 to 2300 nm were also performed. Photographs of frequency-upconverted PL from the NCs collected at 800, 1200, 1600, 2100 nm displayed in FIG. 23 provide more direct evidence for the occurrence of MEPL processes. The normalized one-photon excited PL spectra and MEPL spectra of the NCs are displayed in FIG. 24, for comparison. As illustrated, the MEPL spectra are on the red side of the one-photon excited PL. Such red-shift of the MEPL spectra with respect to one-photon counterpart has been well reported in traditional semiconductor NCs and can be ascribed to the reabsorption effect and size inhomogeneity.

MEPL measurements have been applied on the MAPbBr$_3$, MAPbBr$_3$/(OA)$_2$PbBr$_4$ and CsPbBr$_3$ NCs at wavelengths ranging from 675 to 2300 nm using the measured $\sigma_2$ values at 800 nm as a standard to determine their MPA cross-sections ($\sigma_n$), thus acquiring the MPA spectra. Through integrating $\Delta f_n$ given by Eq. 2 over the entire laser focused volume and time, we quantify and obtain the MEPL strength $F_n$.

$$F_n = \iiint \Delta f_n = \iiint (1/n) \emptyset \rho \eta \sigma_n [I_i(r,z,t)]^n/(\hbar\omega)^n ds\,dz\,dt \quad (2)$$

Factor 1/n denotes the fact that n-photons are simultaneously absorbed from infrared incident laser beam for generating each fluorophore excitation. Ø is MEPL collection efficiency of the experimental setup, ρ is molar concentration of NCs, η is PLQY and the product of η and $\sigma_n$ is multi-photon action cross-section, a direct measurement of MEPL brightness. $I_i(r,z,t)$ is the incident laser intensity at the small volume of ds·dz in sample at time t. The beam waist at the sample point is $w(d) = w_0 \sqrt{1+d^2/z_0^2}$. d is the distance of the sample to the focal point. $w_0$ is the beam waist of laser beam at the focal point. $z_0$ is the Rayleigh length and is related to $w_0$ by $z_0 = \pi w_0^2/\lambda_0$. Taking account of the fact that NCs contained in 2-mm-thick quartz cuvettes were placed at 3.5 cm from the lens focal point and considering the spatial and temporal profiles of the laser pulses are Gaussian functions, the MEPL signal $F_n$ (n=2, 3, 4, and 5) for 2 PA, 3 PA, 4 PA and 5 PA processes can be derived as:

$$F_2 \approx \pi^{3/2} \emptyset \rho \eta \sigma_2 L \tau_p \omega_0^2 d^2 I_0^2 / [8\sqrt{2} z_0^2 (\hbar\omega)^2] \quad (3)$$

$$F_3 \approx \pi^{3/2} \emptyset \rho \eta \sigma_3 L \tau_p \omega_0^2 d^2 I_0^3 / [18\sqrt{3} z_0^2 (\hbar\omega)^3] \quad (4)$$

$$F_4 \approx \pi^{3/2} \emptyset \rho \eta \sigma_4 L \tau_p \omega_0^2 d^2 I_0^4 / [64 z_0^2 (\hbar\omega)^4] \quad (5)$$

$$F_5 \approx \pi^{3/2} \emptyset \rho \eta \sigma_5 L \tau_p \omega_0^2 d^2 I_0^5 / [50\sqrt{5} z_0^2 (\hbar\omega)^4] \quad (6),$$

respectively. In which the approximation of $1+d^2/z_0^2 \approx d^2/z_0^2$ is taken with the fact that $d^2/z_0^2 \gg 1$. d is distance between sample and focal point of the lens (3.5 cm). $\tau_p$ is laser pulse width at e$^{-1}$ maximum, $I_0$ is laser intensity at the sample position. Through applying the expressions of $F_n$ (n=2, 3, 4, and 5) (Eqs. 3-6) and utilizing the $\tau_2$ values at 800 nm measured by Z-scan as standard, $\sigma_n$ (n=2, 3, 4, and 5) values of MAPbBr$_3$, MAPbBr$_3$/(OA)$_2$PbBr$_4$ and CsPbBr$_3$ NCs can be obtained over wavelength range 675-2300 nm, as shown in FIGS. 17 d & 25 b-d.

Figure 25:
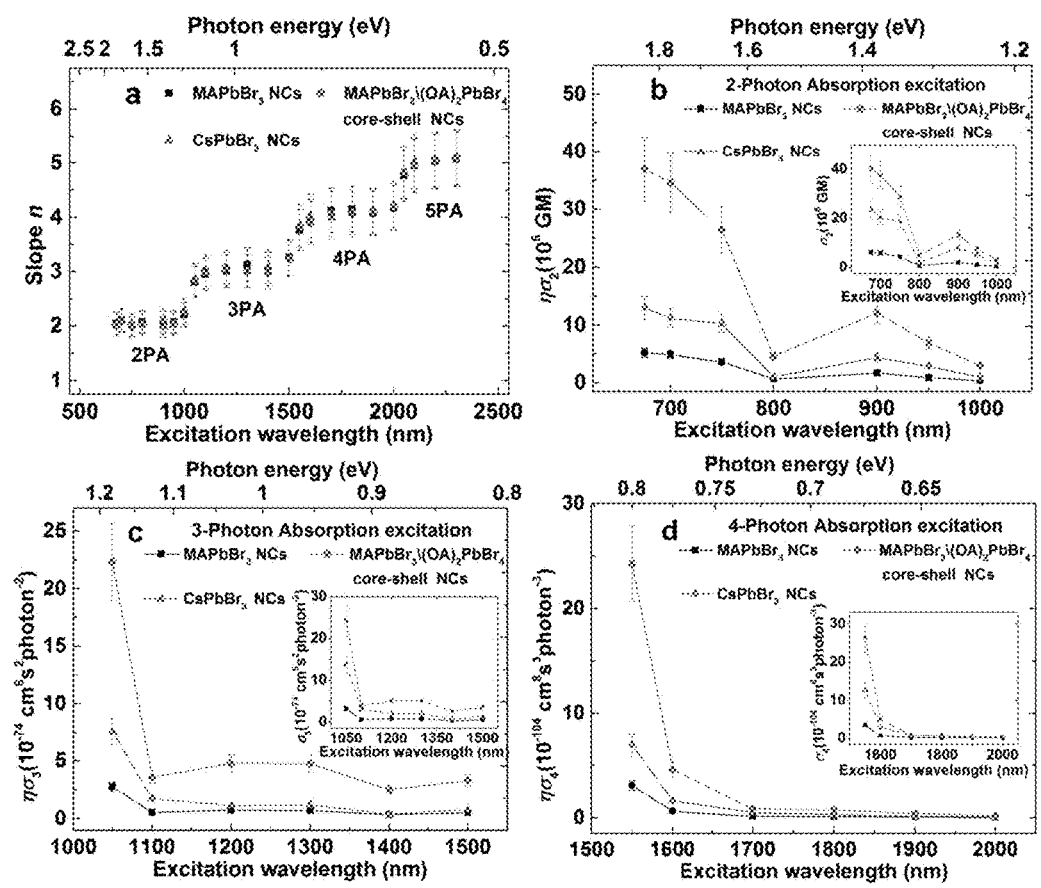
FIG. 25 shows the excitation fluence dependence of multi-photon excited upconversion PL (slopes) as a function of excitation wavelength; and multi-photon action cross-sections ($\eta\sigma_n$) of perovskite NCs. (a) Slopes n plotted as a function of laser excitation wavelength (photon energy), where n is defined as the excitation fluence dependence of the MPPL signal that is proportional to (excitation fluence)$^n$; (b) Two-photon action cross-section ($\eta\sigma_2$) spectra of the MAPbBr$_3$, MAPbBr$_3$/(OA)$_2$PbBr$_4$ and CsPbBr$_3$, NCs in the wavelength range 675-1000 nm; (c) Three-photon action cross-section ($\eta\sigma_3$) spectra of the perovskite NCs in the range 1050-1500 nm; (d) Four-photon action cross-section ($\eta\sigma_4$) spectra of the perovskite NCs in the range 1550-2000 nm. Insets in (b-d) show the corresponding spectral dependence of MPA cross-sections ($\sigma_n$) of the perovskite NCs. Error bars indicate the experimental uncertainty of ±15%.

FIG. 25a shows a summary of the excitation wavelength dependence of the slopes (i.e., orders of multiphoton absorption processes) for these halide perovskite NCs spanning from 675 to 2300 nm. The slopes of PL from the NCs are around 2 in the wavelength range of 675-1000 nm, clearly indicating 2 PA. As the excitation wavelength increases to 1050-1500 nm, the slopes increase to around 3—revealing a switch of the excitation mechanism to 3 PA. 4 PA processes (with slopes around 4) dominate as the excitation wavelength is further increased to the range of 1550-2000 nm. In the long wavelength range 2050-2300 nm, the slopes are around 5, indicating the dominance of 5 PA processes. Due to the NCs size inhomogeneity, $\eta\sigma_n$ at the wavelength boundaries contains an admixture of contributions from both the lower and higher-order MPA process (i.e., 2-/3-PA; 3-/4-PA; and 4-/5-PA etc.). Instead of a sharp transition at the wavelength boundaries (of 1050 nm, 1550 nm and 2050 nm), the slope deviates from the integer value by approximately 20%. FIG. 25 b-d shows a direct comparison of the core MAPbBr$_3$ and core-shell MAPbBr$_3$/(OA)$_2$PbBr$_4$ NCs' MEPL brightness (i.e., $\eta\sigma_n$) to that of CsPbBr$_3$ NCs for lower orders n=2, 3, and 4 over the wavelength range 675-2000 nm. Similar to $\eta\sigma_5$, their spectral dependences exhibit a general overall decreasing trend with increasing wavelength. Their corresponding $\sigma_n$ values are given in FIG. 25 b-d insets. In all these cases, the core-shell MAPbBr$_3$/(OA)$_2$PbBr$_4$ NCs possess ca. 6-8 times larger $\eta\sigma_n$ values than the core-only MAPbBr$_3$ NCs and about 3 times larger $\eta\sigma_n$ values than CsPbBr$_3$ NCs. The $\eta\sigma_n$ spectra suggests that the growth of the 2D (OA)$_2$PbBr$_4$ shell over MAPbBr$_3$ NCs only enhances their MPA and PLQY, while hardly changing their spectral response.

Table 5 complies the elucidated $\eta\sigma_n$ for MAPbBr$_3$, MAPbBr$_3$/(OA)$_2$PbBr$_4$ and CsPbBr$_3$ NCs. Comparatively, the $\eta\sigma_n$ (n=2, 3, 4, and 5) of MAPbBr$_3$ NCs are around 2-3 times smaller than that of CsPbBr$_3$ NCs whereas the core-shell type MAPbBr$_3$/(OA)$_2$PbBr$_4$ NCs exhibit around 3 times larger $\eta\sigma_n$ values than that of CsPbBr$_3$ NCs. Moreover, the $\eta\sigma_2$ values of the core and core-shell type halide perovskite NCs are 1-2 orders larger than that of large size CdSe/CdS dot in rod heterostructures (39 or 180 nm length CdS nanorod, $\eta\sigma_2 \sim (1.1-1.3) \times 10^5$ GM); and are 2-3 orders larger than traditional inorganic semiconductor NCs and organic chromophores (($\eta\sigma_2)_{max} \sim 10^4$ GM). For $\eta\sigma_3$ values, these NCs are 1-2 orders larger than the strongly (or overly) excited ZnSe/ZnS core-shell NCs ($\eta\sigma_3 \sim (3.1-4.1) \times 10^{-76}$ cm$^6$s$^2$ photon$^{-2}$, where three-photon-excited intraband absorption has a significant contribution) and the large CdSe/CdS dot-in-rod heterostructure (39 nm length CdS nanorod, $\eta\sigma_3 \sim (1.9-8.4) \times 10^{-76}$ cm$^6$s$^2$ photon$^{-2}$). The core and core-shell type halide perovskite NCs exhibit $\eta\sigma_3$ values 2-3 orders of magnitude higher than the best performing conventional inorganic semiconductor NCs (that are not overly-excited and with size ≤10 nm) and organic molecules (($\eta\sigma_3)_{max} \sim 10^{-76}$ cm$^6$s$^2$ photon$^{-2}$). For the higher order $\eta\sigma_4$ values, the NCs are about 3-5 orders larger than the best reported results of organic chromophores (($\eta\sigma_4) \sim (1.0 \times 10^{-111}) - (5.6 \times 10^{-109})$ cm$^8$s$^3$ photon$^{-3}$). However, there are only limited research efforts devoted to studying the four-photon process in the conventional inorganic semiconductor NCs. Amazingly, the $\eta\sigma_5$ values of the multidimensional core-shell type NCs are >9 orders larger than specially designed organic molecules ($\eta\sigma_5 \sim 10^{-145}$ cm$^{10}$s$^4$/photon$^4$), which is a record for semiconductor NCs. Although the "Luttinger and Kohn" and "Pidgeon and Brown" models within the k·p approach have been successfully applied to conventional metal-chalcogenide NCs to model their 2 PA/3 PA spectral dependences and estimate their $\sigma_2/\sigma_3$, such approach cannot be directly applied to halide perovskite NCs. This is because these methods are only suitable for the two-photon transitions from s-type valence band to p-type conduction band as in the former, unlike the all p-type valence and conduction bands in the latter. The theoretical study on the MPA properties of the halide perovskite NCs will be the focus of a future work.

Figure 18:
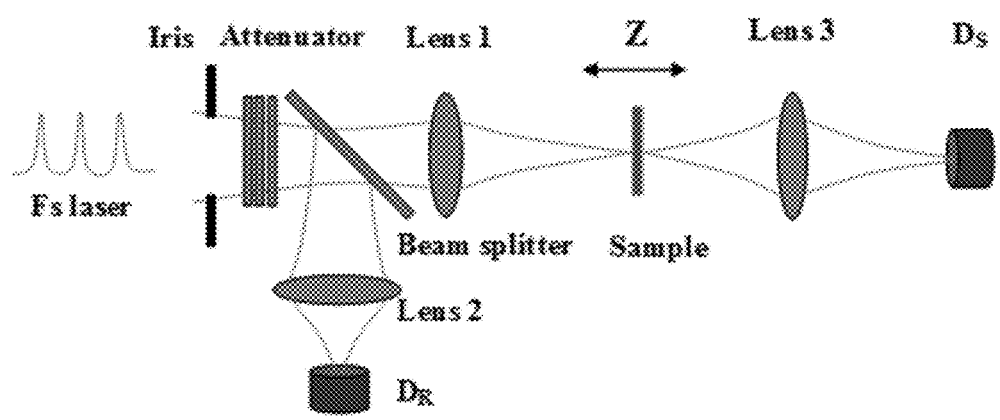
FIG. 18 show a schematic of the open-aperture Z-scan set-up Ds and D$_R$ are the signal power detector (RkP 465, Laser Probe) and reference power detector (RkP 465, Laser Probe), respectively. The signal beam and was focused by a circular lens with 20 cm focus length onto a 1-mm-thick quartz cuvette filled with the toluene solution of perovskite NCs. The transmission of the sample (DS/DR) was monitored while translating the sample through the focal point, and the transmission was recorded as a function of the sample position (z).
Figure 19:
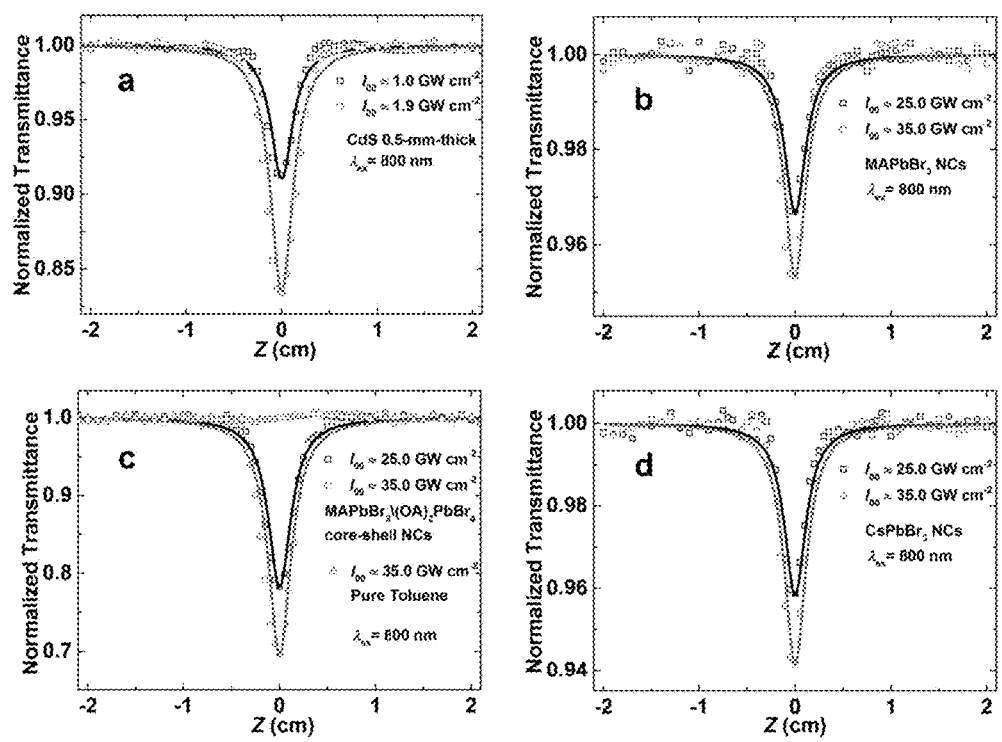
FIG. 19 shows Open-aperture Z-scan measurements (a) Open-aperture Z-scan curves of the standard sample CdS (0.5-mm thick) at 800 nm with peak excitation intensities of ~1.0 and ~1.9 GW cm$^{-2}$; (b-d) Open-aperture Z-scan responses from the toluene solutions of MAPbBr$_3$ (~2.0 µM), MAPbBr$_3$/(OA)$_2$PbBr$_4$ (~2.1 µM) and CsPbBr$_3$ (~1.0 µM) NCs contained in 1-mm-thick cuvette under laser excitation at 800 nm and with peak intensities of ~25.0 and ~35.0 GW cm$^{-2}$. The almost flat open-aperture Z-scan curve of the toluene under the same excitation condition (with peak intensity of ~35.0 GW cm$^{-2}$) is also shown.

Example 10—Open-Aperture Z-Scan Measurements for Quantifying 2 PA Cross-Sections at 800 nm and 3 PA Cross-Sections at 1050 and 1100 nm The 2 PA cross-sections ($\sigma_2$ values at 800 nm) of the colloidal NCs (measured using the open-aperture Z-scan technique) were employed as a standard for multi-photon excited PL (MEPL) measurements at different wavelengths. FIG. 18 illustrates the experimental set-up for the open-aperture Z-scan measurements. A wide-gap semiconductor CdS was utilized as the standard sample for the calibration of the open-aperture Z-scan set-up. FIG. 19 a illustrates the measured open-aperture Z-scan curves on the 0.5-mm thick CdS wafer at 800 nm. The extracted 2 PA coefficient β~5.9 cm GW$^{-1}$ is in good agreement with both theoretical prediction and experimental report, indicating that the set-up is properly calibrated. The open-aperture Z-scan responses of the toluene solutions of MAPbBr$_3$ (~2.0 µM) and MAPbBr$_3$/(OA)$_2$PbBr$_4$ (~2.1 µM) in 1-mm-thick cuvette acquired at 800 nm are presented in FIG. 19 b,c, respectively. Open-aperture Z-scan curves of the CsPbBr$_3$ NCs dispersed in toluene (~1.0 µM) were studied under the same excitation condition for comparison purpose, as displayed in FIG. 19 d. Furthermore, open-aperture Z-scan measurement on the pure toluene solvent was conducted under the same excitation condition as the control experiment, as shown in FIG. 19 c. The almost flat open-aperture Z-scan curve of the toluene suggests its negligible nonlinear absorption response at the applied excitation condition.

2 PA cross-sections ($\sigma_2$) of the NC solutions can be obtained through fitting the normalized transmittance to the well-established Z-scan theory as:

$$T(z) = \frac{(1-R)^2}{\sqrt{\pi}\,q(z)} \int_{-\infty}^{\infty} \ln\left[1 + q(z)e^{-x^2}\right] dx \tag{7}$$

$q(z)=(1-R)\beta I_{00}L_{eff}/(1+z^2/z_0^2)$, $\beta=N\sigma_2/(\hbar\omega)$. R is reflection from the sample front surface; $I_{00}$ is peak intensity at the focal point of the incident laser beam; $L_{eff}=L$ at 800 nm and L is sample thickness due to the negligible 1 PA at this wavelength; N is concentration of NCs; ℏω is the incident photon energy. $\sigma_2$ of the MAPbBr$_3$, and MAPbBr$_3$/(OA)$_2$PbBr$_4$ at 800 nm were estimated to be approximately $(0.8\pm0.1)\times10^6$ GM and $(5.0\pm0.8)\times10^6$ GM, respectively. On the other hand, the $\sigma_2$ value of the CsPbBr$_3$ NCs at 800 nm was derived to be around and $(2.0\pm0.3)\times10^6$ GM, in agreement with literature reports. Taking account of both the volume and the local field effects, the elucidated $\sigma_2$ value of the MAPbBr$_3$ NCs, is about three-orders of magnitude larger than the result corresponding to the recently reported 2 PA coefficient of bulk MAPbBr$_3$ crystal ($\sigma_2$ corresponding to the bulk MAPbBr$_3$ crystal is derived with dielectric constants of toluene and MAPbBr$_3$ ($\varepsilon_0$=2.38 and $\varepsilon$=25.5, respectively)). Such large enhancement results from the quantum confinement effect, which has been well-documented in conventional semiconductor NCs. Moreover, the shell coating with (OA)$_2$PbBr$_4$ has further enhanced the 60 of the MAPbBr$_3$/(OA)$_2$PbBr$_4$ NCs at 800 nm by ~6.5 times. The ratio between the acquired $\sigma_2$ values of MAPbBr$_3$, MAPbBr$_3$/(OA)$_2$PbBr$_4$ and CsPbBr$_3$ NCs at 800 nm is consistent with that obtained from the two-photon-excited PL measurements (FIG. 19, 21 a, 22 a) further validate the experimental approach.

Moreover, the good agreement of the measured 3 PA cross-sections with those acquired from open-aperture Z-scan measurements at 1050 and 1100 nm (see FIG. 21 b, 22 b, 26, 27) further confirms that the MPA cross-sections have been properly measured with the MEPL technique. The applied experimental set-up is similar to the one used for 2 PA at 800 nm. The calibration of the open-aperture Z-scan measurements for 3 PA at 1050 and 1100 nm was conducted utilizing the wide-gap semiconductor CdS. Open-aperture Z-scan curves on the CdS wafer at 1050 and 1100 nm are displayed in FIGS. 26 a and 27 a. Based on the open-aperture Z-scan theory for 3 PA, $Ln(1-T_{OA})$ (where $T_{OA}$ is the normalized transmittance along Z-axis) was plotted as a function of $Ln(I_0)$ ($I_0=I_{00}/(1+z^2/z_0^2)$) at both wavelengths to demonstrate the presence of 3 PA, as shown in insets of FIGS. 26 a and 17 a. The linear fit with slopes of about 1.95 and 2.03 are indicative of the occurrence of 3 PA processes at both wavelengths. The extracted 3 PA coefficients $\gamma(1050\ nm)\sim(1.4\pm0.2)\times10^{-2}\ cm^3GW^{-2}$ and $\gamma(1100\ nm)\sim(1.3\pm0.2)\times10^{-2}\ cm^3GW^{-2}$ agree well with both the experimental report and theoretical calculation, indicating that the Z-scan set-up is properly calibrated.

Figure 26:
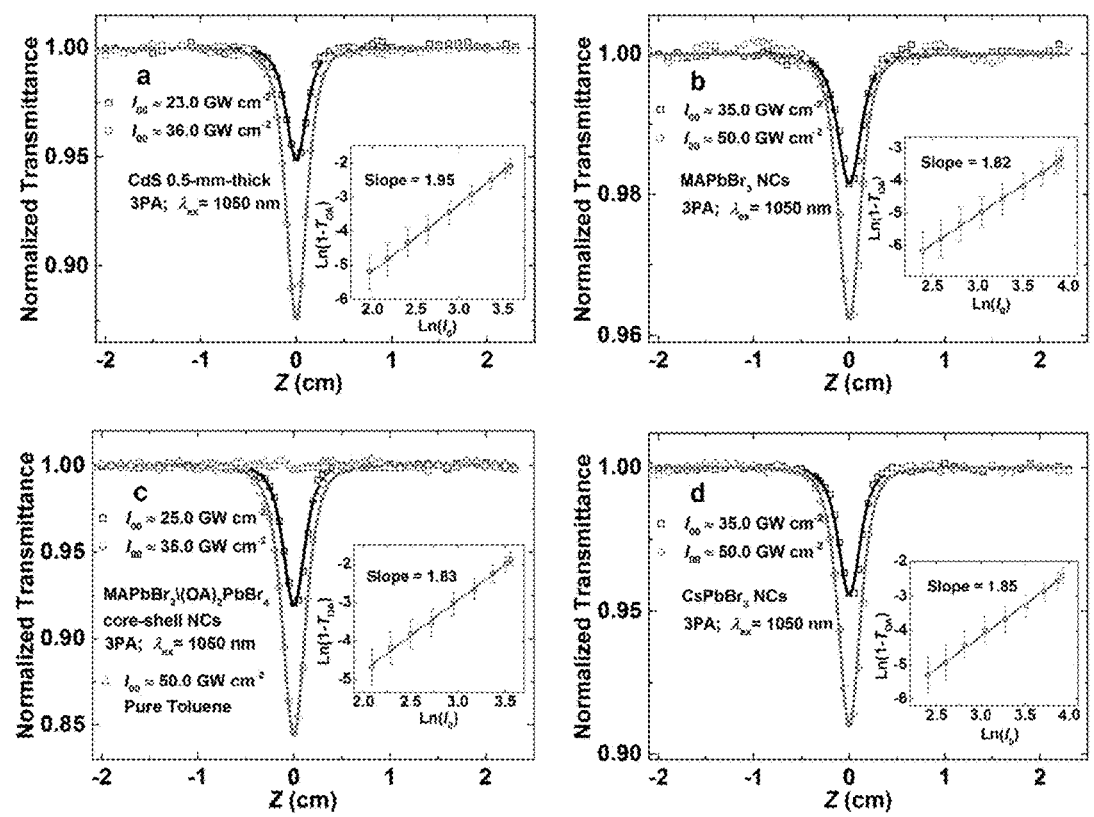
FIG. 26 shows open-aperture Z-scan measurements on 3 PA in perovskite NCs at 1050 nm (a) Open-aperture Z-scan curves of the standard sample CdS (0.5-mm thick) at 1050 nm with excitation peak intensities of ~23.0 and ~36.0 GW cm$^{-2}$; (b) Open-aperture Z-scan responses from the toluene solutions of MAPbBr$_3$ NCs (~2.0 µM) contained in 1-mm-thick cuvette under laser excitation with peak intensities of ~35.0 and ~50.0 GW cm$^{-2}$; (c) Open-aperture Z-scan responses from MAPbBr$_3$/(OA)$_2$PbBr$_4$ NCs (~2.1 µM) excited with peak intensities of ~25.0 and ~35.0 GW cm$^{-2}$.

FIG. 26 b,c show the open-aperture Z-scan responses of 3 PA in the toluene solutions of MAPbBr$_3$ (~2.0 μM) and MAPbBr$_3$/(OA)$_2$PbBr$_4$ NCs (~2.1 μM) in 1-mm-thick cuvette under excitation at 1050 nm. In comparison, the open-aperture Z-scan responses of 3 PA at 1050 nm in toluene solution of CsPbBr$_3$ NCs (~2.0 μM) contained in 1-mm-thick cuvette were acquired, as shown in FIG. 26 d. The insets of FIG. 26 b-d show the corresponding plots of $Ln(1-T_{OA})$ vs. $Ln(I_0)$ together with the linear fits, manifesting the presence of 3 PA. The acquired slopes are about 1.82, 1.83 and 1.85 for MAPbBr$_3$, MAPbBr$_3$/(OA)$_2$PbBr$_4$ and CsPbBr$_3$ NCs, respectively, indicating relatively larger deviation from 2 (i.e., 15-20%). Such deviation at 1050 nm is in accordance with the obtained slopes from the excitation fluence dependence of multi-photon excited upconversion PL (FIG. 25 a). And the deviation may result from the NCs size inhomogeneity leading to an admixture of contributions from both the 2 PA and 3 PA processes at this boundary wavelength of 1050 nm. However, since the deviation is less than 20%, 3 PA process still dominates at this boundary wavelength. For excitation at 1100 nm, open-aperture Z-scan curves of 3 PA in the MAPbBr$_3$ and MAPbBr$_3$/(OA)$_2$PbBr$_4$ NCs in toluene solution were acquired and shown in FIG. 27 b,c. The open-aperture Z-scan curves of 3 PA in the CsPbBr$_3$ NCs were displayed in FIG. 27 d for comparison. Corresponding plots of $Ln(1-T_{OA})$ vs. $Ln(I_0)$ and the linear fits are displayed in insets of FIG. 27 b-d, respectively, to validate the occurrence of the 3 PA processes. The slopes obtained at 1100 nm are about 1.97, 2.03 and 2.01 for MAPbBr$_3$, MAPbBr$_3$/(OA)$_2$PbBr$_4$ and CsPbBr$_3$ NCs, respectively, clearly indicating only 3 PA process occurs at 1100 nm excitation. Open-aperture Z-scan measurements on the pure toluene solvent under the maximum excitation peak intensities at both wavelengths show almost flat response (FIGS. 26 c and 27 c). These results suggest its negligible nonlinear absorption response at the applied excitation conditions.

To acquire the 3 PA cross-sections of the NC solutions, the below well-established Z-scan theory were applied to fit the normalized open-aperture Z-scan transmittance:

$$T(z) = \frac{1}{\sqrt{\pi}\, p_0(z)} \int_{-\infty}^{\infty} \ln\left\{\left[1 + p_0^2(z)e^{-2x^2}\right]^{1/2} + p_0(z)e^{-x^2}\right\} dx \qquad (8)$$

$p_0(z)=(2\gamma(1-R)^2 L'_{\mathit{eff}} I_{00}{}^2/(1+z^2/z_0{}^2)^2)^{1/2}$, $\gamma=N\sigma_3/(\hbar\omega)^2$. $L'_{\mathit{eff}}=L$ at 1050 and 1100 nm and L is sample thickness; $\sigma_3$ is the 3 PA cross-section. 3 PA cross-sections ($\sigma_3$) of the MAPbBr$_3$, MAPbBr$_3$/(OA)$_2$PbBr$_4$ and CsPbBr$_3$ NCs at 1050 nm were estimated to be approximately $(2.3\pm0.3)\times10^{-74}\ cm^6s^2\ photon^{-2}$, $(20\pm3)\times10^{-74}\ cm^6s^2\ photon^{-2}$ and $(6.7\pm1.0)\times10^{-74}\ cm^6s^2\ photon^{-2}$, respectively. Moreover, for excitation at 1100 nm, the 3 PA cross-sections ($\sigma_3$) of the MAPbBr$_3$, MAPbBr$_3$/(OA)$_2$PbBr$_4$ and CsPbBr$_3$ NCs were calculated to be approximately $(0.55\pm0.08)\times10^{-74}\ cm^6s^2\ photon^{-2}$, $(3.3\pm0.5)\times10^{-74}\ cm^6s^2\ photon^{-2}$ and $(1.9\pm0.3)\times10^{-74}\ cm^6s^2\ photon^{-2}$. The obtained $\sigma_3$ of perovskite NCs through the open-aperture Z-scan measurements are highly consistent with the results acquired from multiphoton excited upconversion PL measurements (FIG. 25 c and Table 5) with the variation in the range of about 6%-17%. Hence, the open-aperture Z-scan measurements on 3 PA in the perovskite NCs performed at 1050 and 1100 nm further confirm the 3 PA results measured with the multiphoton excited upconversion PL technique. The good agreement of the 2 PA and 3 PA cross-sections acquired by the multiphoton excited upconversion PL technique with that obtained from open-aperture measurements validates that the multiphoton absorption cross-sections of the perovskite NCs have been properly measured with the multiphoton excited upconversion PL technique.

The core and core-shell organic-inorganic halide perovskite NCs possesses much higher $\eta\sigma_n$ values than those of traditional inorganic semiconductor NCs and organic chromophores (Table 5), highlighting their potential for nonlinear optics and bioimaging applications, such as optical limiting, three-dimensional microscopy for deep tissue imaging and sensing. Moreover, the core-shell organic-inorganic halide perovskite NCs demonstrate larger (about 3 times) $\eta\sigma_n$ values than the new two-photon absorbing benchmark of CsPbBr$_3$ NCs. Apart from having high PLQY (i.e., $\eta\sim84\%$, 92% for MAPbBr$_3$ and MAPbBr$_3$/(OA)$_2$PbBr$_4$ NCs, respectively), these lead bromide perovskite NCs also possess giant σ values, which stems mainly from the intrinsic strong MPA of lead bromide perovskites. Through growing a (OA)$_2$PbBr$_4$ shell over the MAPbBr$_3$ core, the PLQY can be enhanced to ~92% and the photostability can be improved. Most importantly, the presence of the (OA)$_2$PbBr$_4$ shell enhances the $\sigma_n$ by almost an order compared to the core-only MAPbBr$_3$ NCs across all wavelengths from 675 to 2300 nm. Given that both the MAPbBr$_3$ and MAPbBr$_3$/(OA)$_2$PbBr$_4$ NCs are in the weak confinement regime ($d_B\sim4$ nm<<8-9 nm diameter), it is possible to enhance these $\sigma_n$ values even further through even smaller strongly-confined MAPbBr$_3$ NCs, their core-shell counterparts (i.e., NCs' diameter<4 nm). However, at current stage, it is extremely challenging to synthesize small MAPbBr$_3$ and CsPbBr$_3$ NCs with high crystalline quality, low surface defects, uniform size distribution, and relatively high reaction yield, which are needed to conduct detailed investigations of the quantum confinement effect on the MPA of lead bromide perovskite NCs. Presently, there have been no reports on the synthesis of small-sized core-shell MAPbBr$_3$/(OA)$_2$PbBr$_4$ NCs. Therefore, investigation on the detailed dependence of MPA on the quantum confinement effect will one of the main future works.

Example 11—Time-Resolved PL Measurements and Discussion on the Underlying Physical Mechanisms for the Largely Enhanced Multiphoton Action Cross-Sections of the Multi-Dimensional Core-Shell Perovskite NCs Previous studies on conventional inorganic semiconductor NCs have shown that the 2 PA and 3 PA cross-sections can be enhanced by an outer shell covering through: surface passivation effects; antenna-like effect; photoinduced screening of the internal field; and/or local field effects. To establish the origins for the $\sigma_n$ enhancement of the core-shell MAPbBr$_3$/(OA)$_2$PbBr$_4$ NCs and to gain more insights into the dynamics of excited photocarriers, time-resolved PL (TRPL) measurements using single (400 nm) and multi-photon (e.g., 2P (800 nm), 3P (1200 nm), 4P (1600 nm) and 5P (2100 nm)) excitation were performed. FIG. 28 a-c shows the one-photon excited and multi-photon excited TRPL decay lifetimes for the MAPbBr$_3$, MAPbBr$_3$/(OA)$_2$PbBr$_4$ and CsPbBr$_3$ NCs, respectively. For the respective MAPbBr$_3$ and CsPbBr$_3$ NCs, their PL decay curves are almost invariant for one-photon and multi-photon excitation (FIG. 28 a,c), indicating excitation via virtual states to the same lowest excited state in these perovskite NC systems.

The increased PL lifetimes (from one- and multi-photon excitation—FIG. 28 b) together with the enhanced PLQY and stability in MAPbBr$_3$/(OA)$_2$PbBr$_4$ NCs points to the effective surface passivation provided by (OA)$_2$PbBr$_4$ shell that reduces nonradiative surface traps, hence increasing multi-photon transition probability. Furthermore, the longer one- and multi-photon excited PL lifetime, the good spectral overlap between shell emission and core excitation (as revealed in FIG. 29), as well as the intimate proximity between core and shell strongly suggest the presence of non-radiative Förster-type energy transfer from the shell to core through an antenna-like effect. This is another plausible origin for the enhanced $\sigma_n$ in the core-shell MAPbBr$_3$/(OA)$_2$PbBr$_4$ NCs. The 2 PA property of the (OA)$_2$PbBr$_4$ shell revealed by open-aperture Z-scan measurements in FIG. 30 further supports this interpretation. The non-radiative energy transfer from the shell to core enhances the PL from the MAPbBr$_3$ NCs core, resulting in an overall increase of the PL lifetime. The longer multi-photon excited PL lifetime compared to the one-photon excited PL lifetime in MAPbBr$_3$/(OA)$_2$PbBr$_4$ NCs (FIG. 28 b) indicates a larger contribution from this non-radiative energy transfer channel to the resulting core PL, suggesting a more effective non-radiative energy transfer under nonlinear optical excitation.

Next, the relatively large lattice mismatch between the core MAPbBr$_3$ and shell (OA)$_2$PbBr$_4$ could also induce intrinsic piezoelectric polarization charges at the core-shell interface that result in an internal electric field. This indicates that the photoinduced screening of the internal field by the photoexcited electron-hole pairs could be another possible origin for the enhanced $\sigma_n$ in MAPbBr$_3$/(OA)$_2$PbBr$_4$ NCs. Furthermore, the dielectric confinement (local field effect) resulting from the relatively large difference between the dielectric constants of core MAPbBr$_3$ and shell (OA)$_2$PbBr$_4$ could be another factor. Therefore, it is likely that an interplay of various factors arising from the effective surface passivation, the nonradiative energy transfer from the shell to the core through antenna-like effect, the photoinduced screening of the internal field, the local field effect or its combination gives rise to the giant MPA cross-sections of these core-shell multidimensional halide perovskites NCs.

The outstanding higher order nonlinear optical properties of the core and core-shell organic-inorganic halide perovskite colloidal NCs (particularly the highly efficient five-photon excited upconversion fluorescence in the multidimensional core-shell perovskite NCs (e.g., MAPbBr$_3$/(OA)$_2$PbBr$_4$)) indicate their great potential for developing next generation highly efficient, sensitive multiphoton imaging applications with unmatched imaging depth and resolution. Although the intrinsic low stability of halide perovskite NCs in polar solvents (such as water) and their cytotoxicity from the Pb$^{2+}$ ion could be an issue for the potential applications in multi-photon bio-imaging, such technical challenges could be circumvented through the following three possible encapsulation approaches:

First, Encapsulation with an SiO$_x$/SiO$_2$ Inert Shell/Matrix.

Utilizing SiO$_x$/SiO$_2$ either as an additional shell or as a medium to embed several NCs will help to enhance the stability as well as reduce the cytoxicity. Such approach has been successfully applied to traditional inorganic semiconductor NCs for efficient bio-imaging applications. Very recently, encapsulating lead bromide NCs into a SiO$_x$ spherical matrix (about 150 nm and 470 nm in diameter) have been realized by Huang et al. This provides a crucial proof-of-concept on the viability of the approach, although more work is required to achieve finer control of SiO$_x$/SiO$_2$ encapsulation for each perovskite NC.

Second, Encapsulation with Ligands.

Through utilizing 3-aminopropyltriethoxysilane (APTES) as a branched capping ligand to replace the conventional straight-chained ligands, Luo et al. achieved enhanced stability in the APTES-coated MAPbBr$_3$ NCs. Such APTES-coated MAPbBr$_3$ NCs show an increased stability in 2-propanol. Furthermore, the available silane group allows for additional sol-gel reactions which may further increase the stability of the NCs.

Third, Encapsulation with Solid Lipid Structures.

More recently, Gomez et al. reported the application of solid lipid structures to encapsulate CsPbBr$_3$ NCs that were stable up to 2 months in water, albeit at a low PLQY (around 11%) likely due to initial water degradation. Further work is needed to circumvent the initial degradation and realize water-stable NCs at high PLQY.

Fourth, Encapsulation in the Voids of Porous Metal-Organic Frameworks.

The core and core-shell nanocrystals may be further encapsulated in the voids of porous metal-organic frameworks, such as Cu$_3$(1,3,5-benzene tricarboxylate)$_2$ (HKUST-1), Zn$_4$O nodes with 1,4-benzodicarboxylic acid struts (IR-MOF-1), other IRMOF series (like IRMOF-10 and IRMOF-16), zinc ions coordinated by four imidazolate rings (ZIF-8), UiO-66 made up of [Zr$_6$O$_4$(OH)$_4$] clusters with 1,4-benzodicarboxylic acid struts, etc. to enhance the multiphoton absorption property and improve stability and biocompatibility.

These examples clearly show that the potential stability and cytotoxicity issues of halide perovskite NCs in aqueous media for multiphoton imaging applications could in fact be overcome through a judicious choice of the encapsulation approach and careful optimization. Through tuning the emission wavelengths to the infrared by developing appropriate synthesis strategy, these halide perovskite colloidal nanocrystals could enable even deeper imaging for deep-tissue bio-imaging, where both penetration of incident photons and extraction of emitting photons are essential.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A nanocrystal comprising a core comprised in a shell, wherein the core comprises a first perovskite structure, wherein the first perovskite structure comprises a first organic cation not exceeding a molar weight of about 45 g/mol, a first divalent metal and a first counter anion, and wherein the shell comprises a second perovskite structure, wherein the second perovskite structure comprises a second organic cation having a molar weight between about 74 g/mol and about 187 g/mol, optionally the first organic cation, a second divalent metal and a second counter anion,
   wherein the first organic cation and the second organic cation each comprise an ammonium ion, and
   wherein the second organic cation comprises at least one alkyl moiety.

2. The nanocrystal of claim 1, wherein the ammonium ion is independently selected from the group consisting of a primary, a secondary, a tertiary and a quaternary ammonium ion.

3. The nanocrystal of claim 1, wherein the first organic cation comprises at least one alkyl moiety.

4. The nanocrystal of claim 1, wherein the first organic cation comprises an imine moiety.

5. The nanocrystal of claim 1, wherein the first perovskite structure material comprises material of the general formula $(S—NH_3)MX_3$ and wherein the second material comprises material of the general formula $(C_{4-12}\text{-Alk-}NH_3)_2(S—NH_3)_{n-1}M_nX_{3n+1}$ wherein
   S is $—CH_3$ or $—CH=NH$;
   n is an integer selected from 1 to 4;
   M is a divalent metal; and
   X is a counter anion.

6. The nanocrystal of claim 1, wherein the first organic cation and the second organic cation each comprises at least one alkoxysilane.

7. The nanocrystal of claim 1, wherein the second organic cation in the second perovskite structure is configured to separate the second divalent metal from the second counter anion, thereby increasing the d-spacing.

8. The core-shell nanocrystal of claim 1, wherein the first and/or second counter anion is a halogen.

9. The nanocrystal of claim 1, wherein the first and/or second divalent metal is a heavy metal.

10. The nanocrystal of claim 1, wherein the elements of the second perovskite structure are arranged in a substantially 2-dimensional layer.

11. The nanocrystal of claim 1, wherein the nanocrystal is spherical.

12. The nanocrystal of claim 1, wherein the nanocrystal has a diameter of about 1-50 nm.

13. The nanocrystal of claim 1, wherein the nanocrystal is further encapsulated in $SiO_x$ and/or $SiO_2$.

14. The nanocrystal of claim 1, wherein the nanocrystal is further encapsulated with solid lipid structures.

15. A matrix having a nanocrystal of claim 1 encapsulated therein.

16. The nanocrystal of claim 1, wherein the second perovskite structure comprises the second organic cation having a molar weight between about 74 g/mol and about 187 g/mol, and the first organic cation, not exceeding a molar weight of about 45 g/mol, a second divalent metal and a second counter anion.

17. A process for the synthesis of a nanocrystal comprising a core comprised in a shell, wherein the core comprises a first perovskite structure and wherein the shell comprises a second perovskite structure, the process comprising a) preparing a precursor solution containing at least one divalent metal, a first organic cation not exceeding a molar weight of about 45 g/mol, a second organic cation having a molar weight between about 74 g/mol and about 187 g/mol, and at least one counter anion in a polar aprotic solvent; and b) subjecting the precursor solution to a non-polar solvent to form the nanocrystal comprising a core comprised in a shell,
   wherein the first organic cation and the second organic cation each comprise an ammonium ion, and
   wherein the second organic cation comprises at least one alkyl moiety.

18. The process for the synthesis of a nanocrystal of claim 17, wherein the molar ratio of the first organic cation to the second organic cation is in the range of 9:1 to 1:9.

19. The process for the synthesis of a nanocrystal of claim 17, wherein the formation of the nanocrystal proceeds in a 'one-pot' process.

* * * * *